United States Patent [19]

Matsen, III et al.

[11] Patent Number: 4,979,949
[45] Date of Patent: Dec. 25, 1990

[54] ROBOT-AIDED SYSTEM FOR SURGERY

[75] Inventors: Frederick A. Matsen, III; Joseph L. Garbini; John A. Sidles, all of Seattle; Donald C. Baumgarten, Lynnwood; Brian S. Pratt, Seattle, all of Wash.

[73] Assignee: The Board of Regents of The University of Washington, Seattle, Wash.

[21] Appl. No.: 186,345

[22] Filed: Apr. 26, 1988

[51] Int. Cl.$^5$ .............................................. A61B 17/00
[52] U.S. Cl. ....................................... 606/53; 606/88; 414/9
[58] Field of Search ...................... 606/53, 54, 79, 80, 606/86, 87, 88, 89; 414/9

[56] References Cited

U.S. PATENT DOCUMENTS

| | | | |
|---|---|---|---|
| 4,211,228 | 7/1980 | Cloutier | 128/303 R |
| 4,445,184 | 4/1984 | Noguchi | 364/513 |
| 4,467,801 | 8/1984 | Whiteside | 128/303 R |
| 4,604,016 | 8/1986 | Joyce | 414/7 |

Primary Examiner—Robert A. Hafer
Assistant Examiner—Lynda M. Cofsky
Attorney, Agent, or Firm—Christensen, O'Connor, Johnson & Kindness

[57] ABSTRACT

A system and method for positioning a tool relative to a patient's bone to facilitate the performance of a surgical bone alteration task. The system comprises a bone immobilization device for supporting the bone in a fixed position with respect to a reference structure, and a robot that includes a base fixed in position with respect to the reference structure. The robot also includes a mounting member, and a manipulator connected between the base and the mounting member and permitting relative movement therebetween. The tool to be positioned by the system is mounted to the mounting member. The mounting member is caused to move relative to the reference structure in response to movement commands, so that the tool can be moved to a desired task position to facilitate performance of the task. The system preferably also includes a template attachable to the mounting member, a feature of the template representing a portion of a task. Preferably, the template is secured to the mounting member, and the template is then manually manipulated such that the template feature is properly oriented with respect to the patient's bone. The template position is then recorded as a reference position that may thereafter be combined with a geometric database defining the task to determine the position of the tool. Particular embodiments for a bone immobilizer, a template and a saw guide are also described, together with a stabilizing device for the robot and a safety device for the robot base.

17 Claims, 21 Drawing Sheets

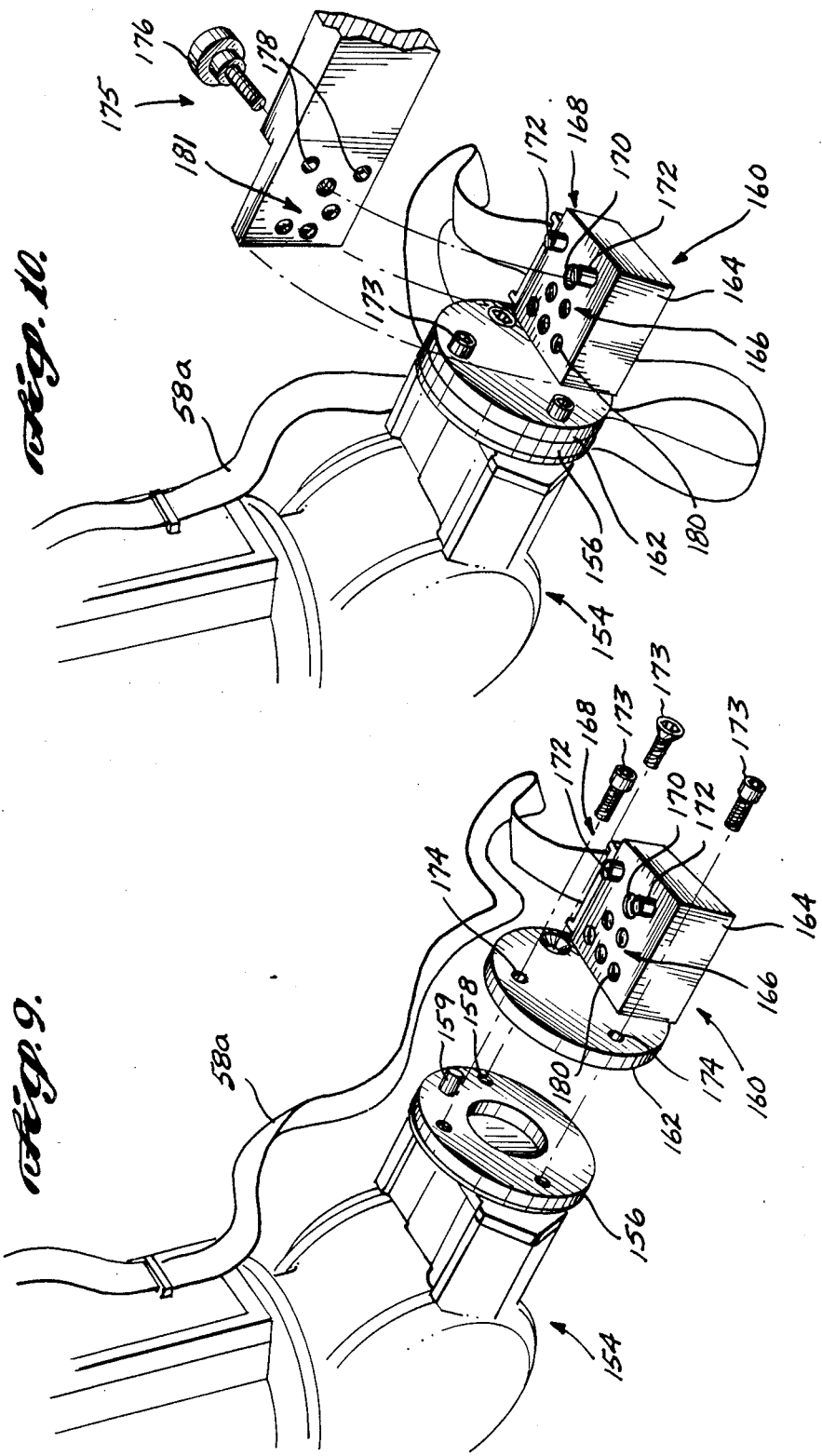

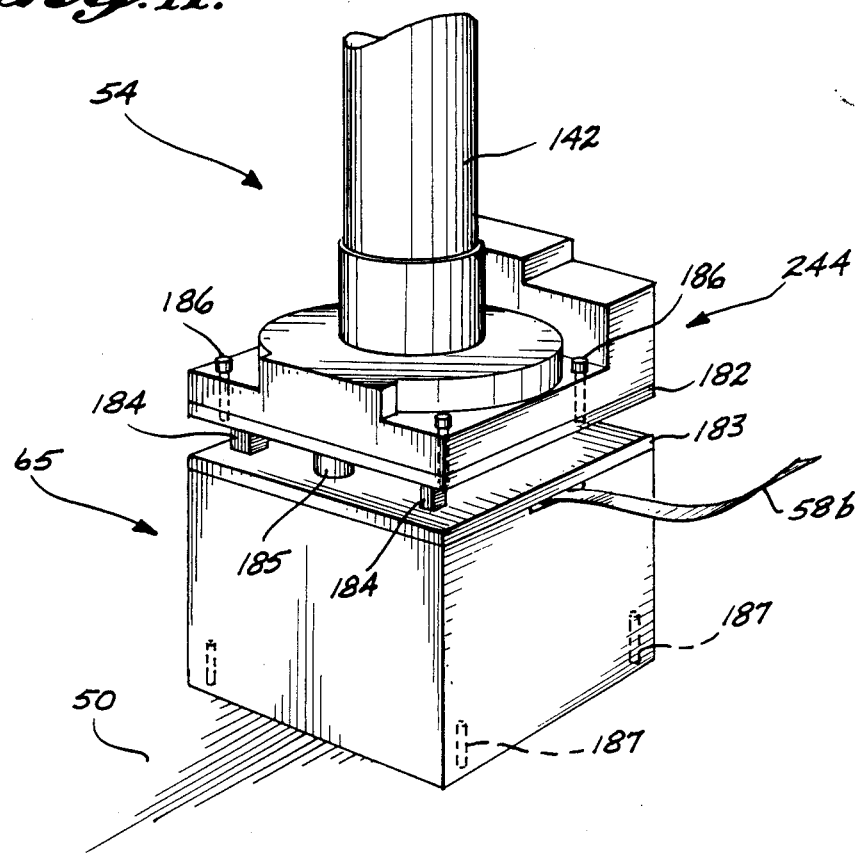
Fig. 11.
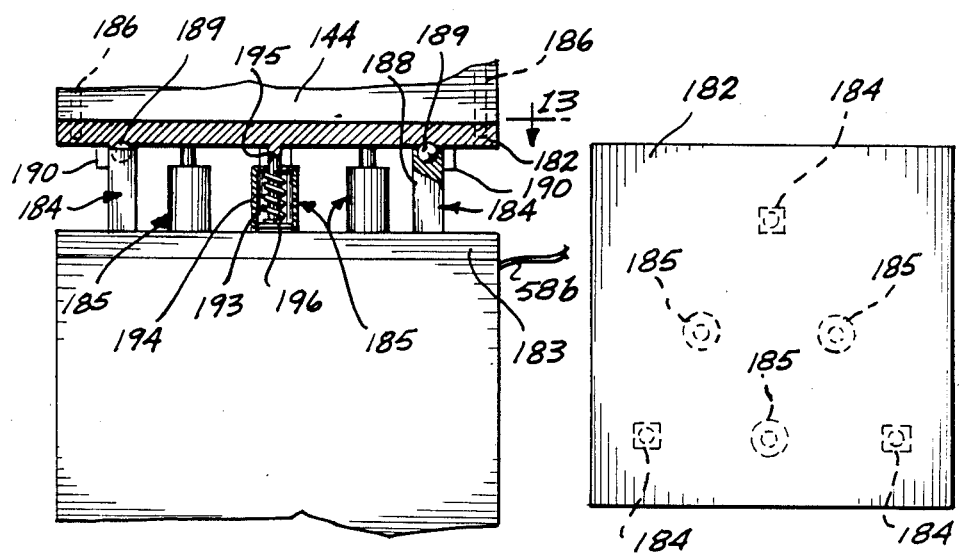
Fig. 12.
Fig. 13.

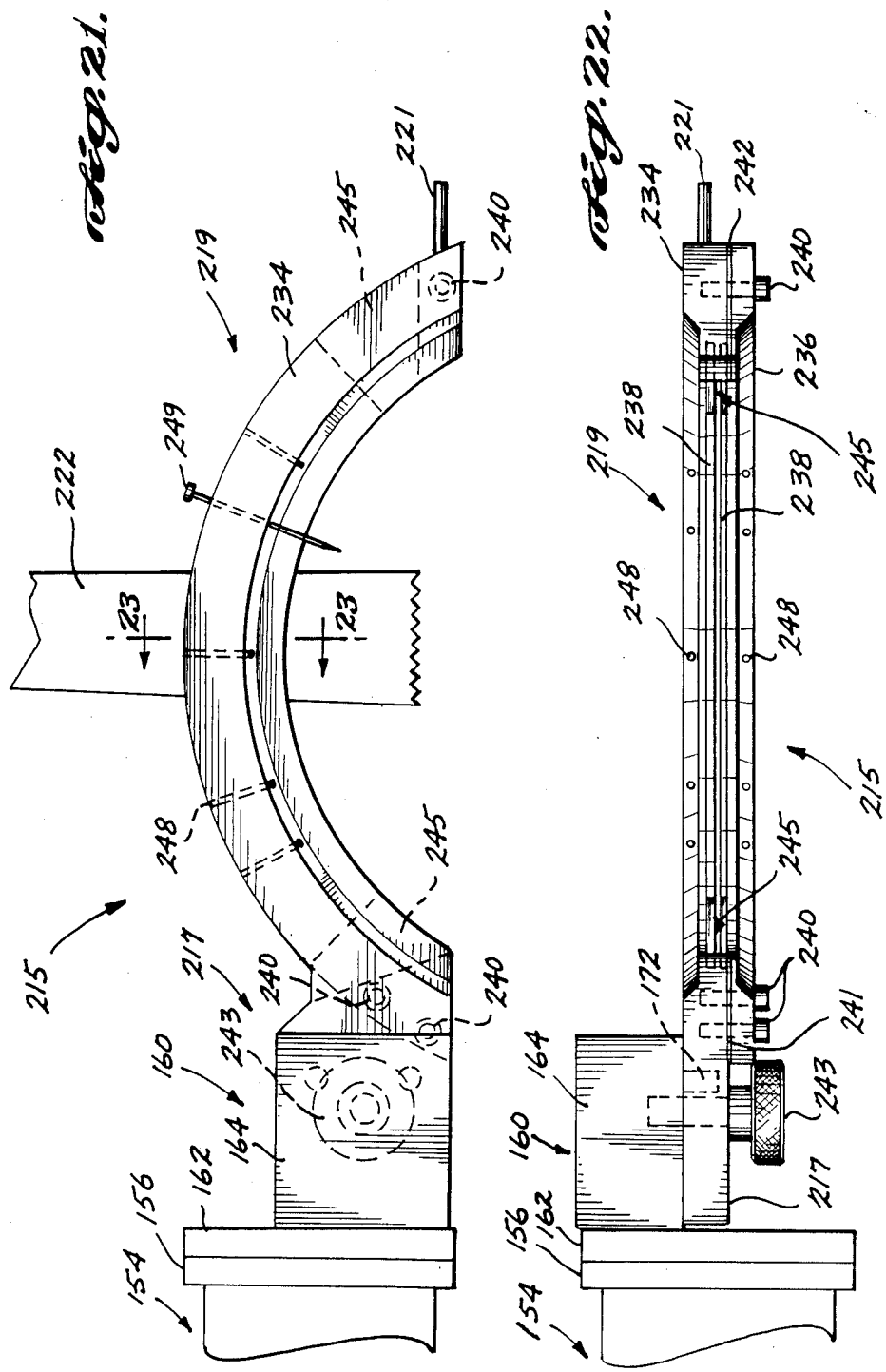

ROBOT-AIDED SYSTEM FOR SURGERY

FIELD OF THE INVENTION

The present invention relates to apparatus and methods applicable in surgical situations in which the precise positioning of a tool in relation to a patient is an integral part of the surgery. More particularly, the present invention utilizes a programmable robot in a system for determining a reference position for certain surgical tasks, precisely determining the position for a specific tool relative to the reference position, positioning the tool, and rigidly holding the tool to aid the surgeon in a more efficient and accurate completion of the task.

BACKGROUND OF THE INVENTION

During orthopedic surgery, it is often the case that surgeons are required to make surgical alterations to bone. Such alterations include but are not limited to making cuts in bone, drilling holes in bone, and affixing a plate, screw, nail, or prosthesis to bone.

When making such alterations, it is desirable that the alteration be realized in a manner which precisely conforms to the operative plan of the surgeon. Among the aspects of a surgical alteration which require careful control are: (1) the alignment of the cut, hole, plate, screw, nail, or prosthesis with respect to the anatomy of the patient; (2) if there is more than one bone cut and/or hole, the relative alignment of the cuts and holes with respect to each other; and (3) if a plate, screw, nail, or prosthesis is to be fixed to bone, the alignment of the cuts and/or holes with respect to the plate, screw, nail or prosthesis.

Current surgical techniques utilize limited mechanical means to assist the surgeon in making bone alterations. However, existing techniques do not suffice to ensure that perfect or nearly perfect alterations can be achieved routinely. Where practical, it is desirable to enhance the surgeon's decision-making process by providing accurate solutions to purely geometric problems posed by surgery, while leaving final positioning decisions up to the surgeon. When the surgeon is provided with accurate geometric solutions, the quality of the overall subjective evaluation should be improved.

An example of a surgical procedure that requires accurate geometric solutions, as well as the evaluation of specific patient physiological characteristics, is total knee arthroplasty (TKA), which is a total knee reconstruction surgery. The anatomic knee is a remarkable mechanism. Contrary to first impression, it is not a simple hinge. Rather, the femur and tibia move relative to each other with a complex mixture of rolling and sliding motions. The stability of the joint comes entirely from soft tissue structures, not from bone geometry. The major stabilizing ligaments are the medial and lateral collateral ligaments, and the anterior and posterior cruciate ligaments.

In total knee arthroplasty, the distal femur and the proximal tibia are resected and are replaced by prosthetic components made of metal and plastic. The most successful designs are unconstrained prostheses that closely mimic the natural anatomy of the knee. Like the anatomic knee, unconstrained designs allow the femur and tibia to roll and slide relative to each other. They depend on the natural ligamentous structures of the knee to stabilize the reconstructed joint.

Total knee reconstruction surgery is conceptually simple. The knee is flexed, the patella moved to one side to give access to the joint, and the degenerated surfaces of the femur and tibia are cut away. The bone cuts are made to fit femoral and tibial prosthetic components, which are available in a wide variety of sizes and styles. These are generally cemented into place, using polymethyl methacrylate (PMMA). One new technique uses no cement. Rather, bone grows into a porous backing on the prosthetic component. This is termed porous-ingrowth fixation.

Each year, approximately 100,000 people undergo a TKA. TKAs are often performed in people whose knees have become so painful, because of progressive arthritic changes, that they are unable to rise from a chair, walk, or climb stairs. For these people, total knee arthroplasty can provide a return to near-normal, pain-free life.

A great deal of developmental technology has gone into perfecting the femur prostheses used in TKAs. However, the technology for positioning the prosthesis properly on the femur has not similarly advanced. Ideally, the bone cuts should be (1) an exact press-fit to the components, and (2) in proper alignment with respect to bones and soft tissues. Failure to achieve these goals will result in poor knee mechanics and/or loosening of the components, leading eventually to failure of the reconstruction.

At present, the surgical instrumentation used in total knee arthroplasty consists of hand-held saws which are guided by simple cutting blocks and mechanical jig systems. There is abundant evidence in the literature that these tools do not suffice to do a good job. First, most prosthetic components are not put in with perfect alignment, and misalignment of three to five degrees or more is not uncommon. Second, prosthetic components do not fit perfectly on the bone, and there are inadvertent gaps between the cut surface of the bone and the prosthesis. Third, there is a learning curve associated with arthroplasty technique. The first fifty knees a surgeon does are not as good as subsequent knees.

The primary goals of the surgeon during total knee arthroplasty are: proper alignment of the reconstructed knee, stability of the reconstructed knee, and press-fit of the components to the bone. With respect to alignment, the knee should neither be knock-kneed or bowlegged, to ensure that the medial and lateral sides of the components bear equal loads. Asymmetric loading leads to early failure. In addition, the ligaments of the knee should provide stability at all angles of flexion, as they do in the anatomic knee. If the ligaments are too tight, they will restrict the motion of the knee. If they are too loose, the knee will "give way" during use.

Finally, if a prosthetic component is even slightly loose, then each step will "rock" the component against the bone. The bone soon gives way, and the reconstruction fails. Ideally, the prosthesis is a press-fit to the cut bone at the time of surgery. This minimizes micro-scale rocking motions. Press-fit is especially important for a porous ingrowth prosthesis, since even a one-millimeter gap between prosthesis and bone is too large for the ingrowth process to bridge.

These goals are simple to state, but difficult to achieve in the operating room. To understand the problems, consideration should be given to all the ways malalignment can occur. There are three different ways a component can be malaligned in orientation. These correspond to rotations of the component away from the desired orientation along the internal/external, varus/valgus, and flexion/extension axes. Similarly, there are three different ways to malposition a component by translation along an axis. These correspond to translations along the medial/lateral, proximal/distal, and anterior/posterior axes.

Thus, to achieve good alignment and good ligament balance, surgeons must mentally manipulate three translational and three orientational variables for each of the femoral and tibial components, or twelve spatial variables in all. Margins for error are small. Repositioning the prosthetic component by even one millimeter has an appreciable effect on the stability of the knee. Moreover, each knee presents its own special problems. It is frequently the case that the knee has a preexisting deformity which must be taken into account.

In addition, the surgeon must also take care that the bone surfaces are press-fit to the component. This involves five cut planes and two drill holes for a typical femoral component, and one cut plane and two drill holes for a typical tibial component, for a total of ten separate cutting operations. In each case, imprecision of one millimeter or less can have significant consequences, especially for porous-ingrowth prostheses.

It is a remarkable fact that present-day surgical instruments for total knee arthroplasty could have been manufactured in the nineteenth century. The essential features of present-day instrumentation systems are their reliance on hand-held oscillating saws to make bone cuts, and mechanical jigs with slots and cutting blocks to help align the cuts. Considerable ingenuity has been applied to optimizing instrumentation systems of this type, and there are dozens of variations on the market. Nonetheless, poor alignment and inaccurate cuts are common problems when using these mechanical instrumentation systems.

Poor alignment occurs when femoral and tibial cutting jigs are not properly aligned with respect to the hip, the ankle, and the stabilizing soft tissues of the knee. This can happen because the surgeon is mislead by the anatomic landmarks used by a given system, because the landmarks are concealed by fat and muscle, because preoperative deformities exist, or because the jig has shifted slightly during the procedure. The best test of alignment is flexion of the newly reconstructed knee. Unfortunately, by the time such a test can be made, the bone cuts have been made, and it is too late to change the alignment of the components.

Inaccurate cuts occur when the various cuts and drill holes do not precisely mate with the surfaces of the prosthetic components, possibly as the result of errors which accumulate during placement and removal of the various cutting blocks. Also, there is inherent inaccuracy associated with a flexible, oscillating saw blade resting on a cutting block or in a slot. The blade tends to "sky" when it encounters a dense section of bone. This tendency is resisted by canting the hand-held saw in a downward direction.

There is ample evidence in the published literature that the present state of total knee arthroplasty is not satisfactory. Cameron H.U., Hunter G.A. in: *Failure in Total Knee Arthroplasty*, 170 Clinical Orthopaedics and Related Research: pp. 141, 146, 1982, noted, "[t]he results of knee arthroplasty range from an acceptable 5.4% failure rate at five years to an abysmal 70% failure rate at three years. Failure rates of this magnitude indicate that many revisions are being performed." Bryan R.S., Rand M.J. in: *Revision Total Knee Arthroplasty*, 170 Clinical Orthopaedics and Related Research: pp. 116–122, 1982, state that, "[p]roper component alignment is of critical importance" and that "[f]ailure to obtain appropriate component orientation, axial alignment, and soft tissue balance predisposes implants to loosening and failure." Hood R.W., Vannie M., and Install J.N., as noted in, *The Correction of Knee Alignment in* 255 *Consecutive Total Condylar Knee Replacements*, 160 Clinical Orthopaedics and Related Research: pp. 94–105, 1981, found in a series of 225 knees that, "[e]leven percent of the knees in this series were outside the alignment limits selected. This may reflect extremes of body habitus but, more importantly, indicates that deficiencies in instrumentation still remain." Hvid I., Nielsen S. in: *Total Condylar Knee Arthroplasty*, 55 Acta Orthop Scand 55: pp. 160–165, 1984, found in a study of 138 knees that although "the aim was to place the tibial component at right angles to the tibial axis," only "53 per cent were within four degrees of tilt in any direction." Some of their components were eight degrees or more out of alignment. In summary, there is ample evidence that with existing instrumentation surgeons cannot obtain good alignment routinely in total knee arthroplasty.

As is evident from the less-than-satisfactory clinical results, the theory and practice of jig-assisted knee surgery are two different things. In practice, total knee arthroplasty is largely a seat-of-the-pants procedure. Surgeons recruit every pair of eyes in the operating room to judge how a contemplated cut "looks" from a variety of angles. Equally important is a steady and practiced hand on the cutting saw, and a sound understanding of the biomechanics of the knee joint.

The conventional TKA requires that the surgeon attempt to achieve exact physiologically correct relationships and to make geometrically exact cuts with inexact methods. As discussed above, both the position and quality of the cuts and bores greatly affect the success of the operation. While the background of a TKA has been described, numerous types of surgeries present the same problem of integrating geometric analysis with a subjective evaluation of physiological factors. Examples of such surgeries are osteotomies and ligament repairs. In the majority of these operations, certain mechanical devices, such as the jig systems described above, have been developed to aid in the operation. The exactness of these mechanical devices varies and, thus, so do the efficiencies resulting from their use. However, most surgical procedures that are not solely based on subjective medical decisions will suffer from some inaccuracies based on the fact that surgeons have a limited capacity for making independent exact geometric calculations and carrying out tasks based on those calculations.

SUMMARY OF THE INVENTION

The object of the present invention is to provide a system and method for facilitating the performance of a surgical bone alternation task by accurately positioning a tool relative to the patient's bone. The illustrative example of a total knee arthroplasty (TKA) of a femur is used.

In one preferred embodiment, a system according to the present invention comprises bone immobilization means and a robot. The bone immobilization means supports the patient's bone in a fixed position with respect to a reference structure. The robot comprises a base, a mounting member and a manipulator. The base is fixed in position with respect to the reference structure.

The manipulator connects the mounting member to the base so as to permit relative movement between the mounting member and the base. The robot also includes attachment means for securing a tool to the mounting member. Finally, the system includes means for causing the mounting member to move relative to the reference structure in response to movement commands, so that the tool can be moved to a position to facilitate performance of the task. The movement commands are preferably provided by task control means that includes memory means for storing data and control programs, and control processing means for processing the control programs to generate the movement commands.

Preferably the system also includes a template attachable to the mounting member. The template may be positioned such that a predetermined feature of the template is in a desired position relative to the bone. For a TKA procedure, the template feature may represent a surface of a prothesis to be mounted on the patient's bone. With the template in the desired position, the reference position of the template is recorded in a "world" coordinate system that is fixed with respect to the reference structure. The reference position may therefore be combined with a geometric database that includes data representing the geometric relationships relevant to the performance of the task, to generate movement commands that cause the robot to move surgical tools into desired tool positions during subsequent stages of the operation. Preferably, the reference position is determined by placing the robot in a passive mode in which the mounting member may be moved manually by an operator. The operator can then mount the template to the mounting member, move the template and mounting member such that the template is properly positioned with respect to the bone, and then cause the system to record the reference position. The robot can then be returned to an active mode in which the mounting member moves in response to movement commands.

The present invention further provides a prosthesis template for aiding in the determination of the desired position and orientation of a prosthesis relative to a bone. The prosthesis has an exterior surface that simulates the exterior surface of the bone and an interior surface comprised of one or more relatively planar surfaces to which the prepared bone must conform. The prosthesis template has a functional interior surface defined by at least three contour lines. This functional interior surface corresponds to the exterior surface of the prosthesis so that when the template is positioned near the bone it provides a means for evaluating the position and orientation of the prosthesis exterior surface relative to the bone.

In accordance with additional aspects of this invention, the prosthesis template includes cut guide marks on the template. The cut guide marks lie in the various planes that correspond to the interior surfaces of the prosthesis, and thus correspond to the bone cuts that must be made in order to prepare the bone for the prosthesis. The relationship between the cut guide marks and the functional interior surface of the template correspond to the relationship between the interior surface and the exterior surface of the prosthesis. Thus, when the template is positioned near the bone, it provides a means for evaluating the position and orientation of the prosthesis interior and exterior surfaces relative to the bone.

In accordance with additional aspects of this invention, a stabilizing device is provided for creating a rigid link between the mounting member and the reference structure, in addition to the link provided by the manipulator. Any compliance of the end of the saw guide is thus prevented so that, for example, the inner surface of the guide is held rigidly within the cut plane throughout the cutting task. The stabilizing device permits use of a smaller and more compact robot in the surgical system.

In accordance with other aspects of this invention, the stabilizing device is incorporated into a safety feature of the task control means. When the mounting member, tool, stabilizing device, and the article to which the stabilizing device is attached are made of electrically conductive materials, the attachment of the mounting member to the stabilizing device produces a simple circuit. The task control means detects when the circuit is complete and will not allow manipulator movement during that time. Thus, the robot will never inadvertently move when the mounting member is stabilized.

In accordance with still further aspects of this invention, the template and tools used in the system include a tool identification pattern that uniquely identifies each tool. An identification device is included in the attachment means so that when the template or tool is mounted, the identification pattern can be read and transferred to the task control means. The identification is then compared to the identification for the template or tool that is appropriate for the task. An error message is generated and displayed if the incorrect template or tool is attached.

In accordance with still other aspects of this invention, the robot base includes a tiltable safety stand, including a means of communicating to the task control means the status of the stand. The safety stand is configured so that if the robot encounters a rigid object while it is moving, the stand will tilt away from the object, thereby preventing the continued force against the object. When the stand tilts, a safety signal is generated that is received by the task control means and is indicative of the need to shut off the power to the robot.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 9 is an isometric view of the wrist and the mounting flange of the robot with the tool-coupling device of the present invention exploded away from the mounting flange;

FIG. 10 is an isometric view of the wrist and coupling device illustrated in FIG. 9 with a sample tool attachment flange shown exploded away from the coupling device;

FIG. 11 is an isometric view of the robot safety stand used in the system illustrated in FIG. 3;

FIG. 12 is a side view of the robot safety stand with portions of the upper plate and one spring assembly cut away to show the compliance features of the stand;

FIG. 13 is a top view of the top plate of the robot safety stand to show the configuration of the upright supports and the spring assemblies;

FIG. 21 is a top view of the saw guide with a saw blade positioned between the guide plates;

FIG. 22 is a front view of the saw guide;

DETAILED DESCRIPTION OF THE PREFERRED EMBODIMENT

The present invention is directed to a system and method for aiding in a surgical procedure that includes the task of determining the precise position and orientation of a tool relative to a reference structure or point. That determination may be in part a geometrical solution and in part a subjective solution based on the physiology of the patient. The system will be described in terms of a total knee arthroplasty (TKA), which is a representative procedure having the above-described characteristics. For illustration, the replacement of the distal end of a femur will be described. The below-described system and method are applicable to similar surgical procedures. It is to be understood that throughout the present application, the use of the term "position" describes both point and orientation information. This is accepted terminology in the area of robotics.

In one preferred embodiment, the present invention provides a two-step method and related apparatus for aiding in surgical procedures. The first step includes the determination of the desired position of a surgical task relative to a bone. In the TKA, the surgical task includes replacing a portion of the bone with a prosthesis. The surgeon is provided with a template having a feature that represents a portion of the prosthesis, such as the prosthesis exterior surface. The surgeon positions the template such that the template feature is in the desired position of the corresponding prosthesis portion, and then causes the template position relative to a fixed point to be recorded. The second step, or bone preparation step, includes determining the position of a tool, e.g., a saw guide or drill guide, relative to the desired prosthesis position. This step also includes actually positioning the tool. A tool position is determined by combining the position of the template with geometric information defining the task; i.e., the prosthesis' characteristics defining the manner in which the bone must be prepared. For example, by determining the position of the anterior cut from the position of the template, the position of the saw blade is also determined; i.e., the blade must be held by the saw guide in the plane of the cut near the bone. This method provides a clear distinction between the prosthesis-positioning step and the bone-preparation step.

Figure 1:
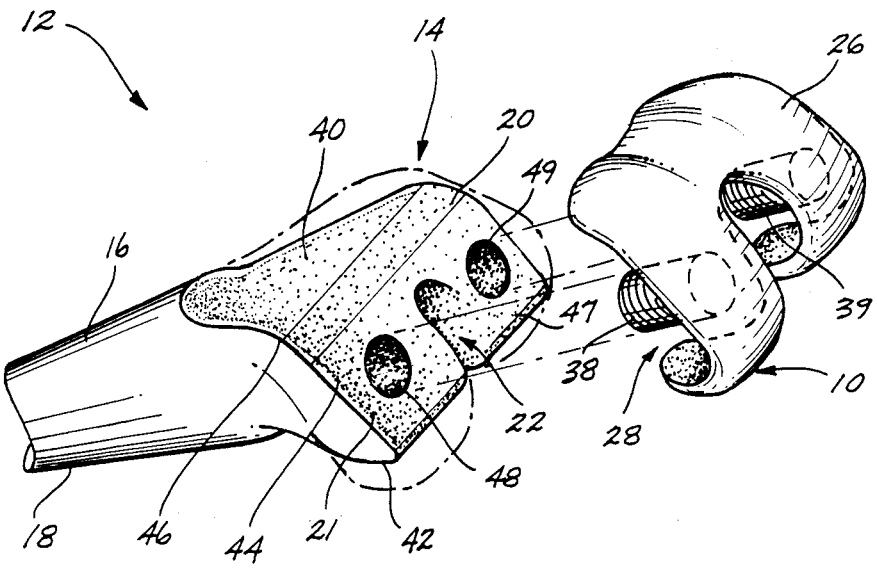
FIG. 1 is an isometric view of a prosthesis and a bone, with the end of the bone prepared to receive the prosthesis.
Figure 2:
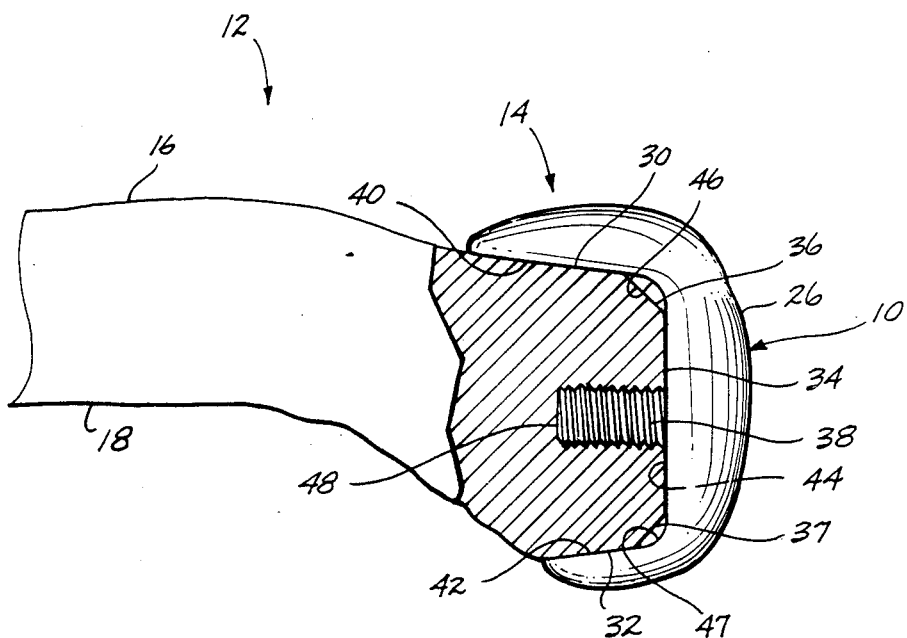
FIG. 2 is a side view of a bone with a prosthesis press fit thereon, with the bone partially cut away to show the prosthesis anchoring stud.

With reference to FIGS. 1 and 2, a prosthesis 10 is used to replace the end of a bone 12 when the bone is damaged or diseased in some way, or is malaligned within the knee joint. The bone 12 may be a femur with the prosthesis 10 fitted onto the distal end 14. Other identifiable portions of the bone are the anterior side 16, the posterior side 18, the condyles 20 and 21, and the notch margin 22. The exterior surface 26 of the prosthesis simulates the distal end of a normal femur, including the condyles and the notch margin.

With respect to gross alignment, the femoral position relative to the knee joint is important. The translational degrees of freedom of the femur are the distal-proximal, anterior-posterior, and medial-lateral directions. Rotations about these axes are referred to as axial, varus-valgus, and flexion-extension, respectively. Femoral prosthesis gross alignment errors include: (1) distal-proximal positioning error, which causes excessive tightness or laxity in the tendons of the knee when the knee is extended; (2) anterior-posterior positioning error, which causes misalignment of the mechanical axes of the femur and tibia; (3) flexion-extension rotation of the prosthesis, which results in excessive flexion or extension of the joint; and (4) varus-valgus rotation of the components, resulting in a knock-kneed or bow-legged effect or the tibial and femoral components meeting in shear. Because there is no exact femur model to follow, and the natural distal end of the femur may not provide a good model, the correct gross alignment of the prosthesis is highly dependent upon the surgeon's subjective evaluation of the knee.

With respect to local fit, the preparation of the femur for the prosthesis is dictated by the configuration of the interior surface 28 of the prosthesis. The geometric relationships that define the bone preparation tasks are the same as the geometric relationships making up the interior surface. The interior surface of the prosthesis is made up of anterior 30, posterior 32, and distal 34 planar surfaces, and chamfers 36 and 37, which are slightly curved. Additionally, two anchoring studs 38 and 39 extend normally from the distal surface 34. In order to prepare the bone, planar cuts are made on the femur that correspond to the interior surfaces of the prosthesis. These cuts result in anterior 40, posterior 42, distal 44, and chamfer 46 and 47 planar surfaces on the femur. The chamfer cuts 46 and 47 can be single-cut planes that provide a relatively tight fit with the curved surfaces 36 and 37 of the prosthesis. Alternatively, multiple chamfer cuts can be made to produce more rounded cut surfaces. Also, stud holes 48 and 49 are drilled to receive the anchoring studs 38 and 39, respectively.

With reference to FIG. 2, after bone preparation, the prosthesis is press-fit onto the femur. The cut surfaces of the bone contact the interior surfaces of the prosthesis.

For each manufacturer, bone type, and size, the configuration of the prosthesis can be determined by taking simple physical measurements. The present system integrates these known geometric relationships between the interior surfaces of the prosthesis with the subjective determination of the surgeon as to the desired gross alignment of the prosthesis.

Figure 3:
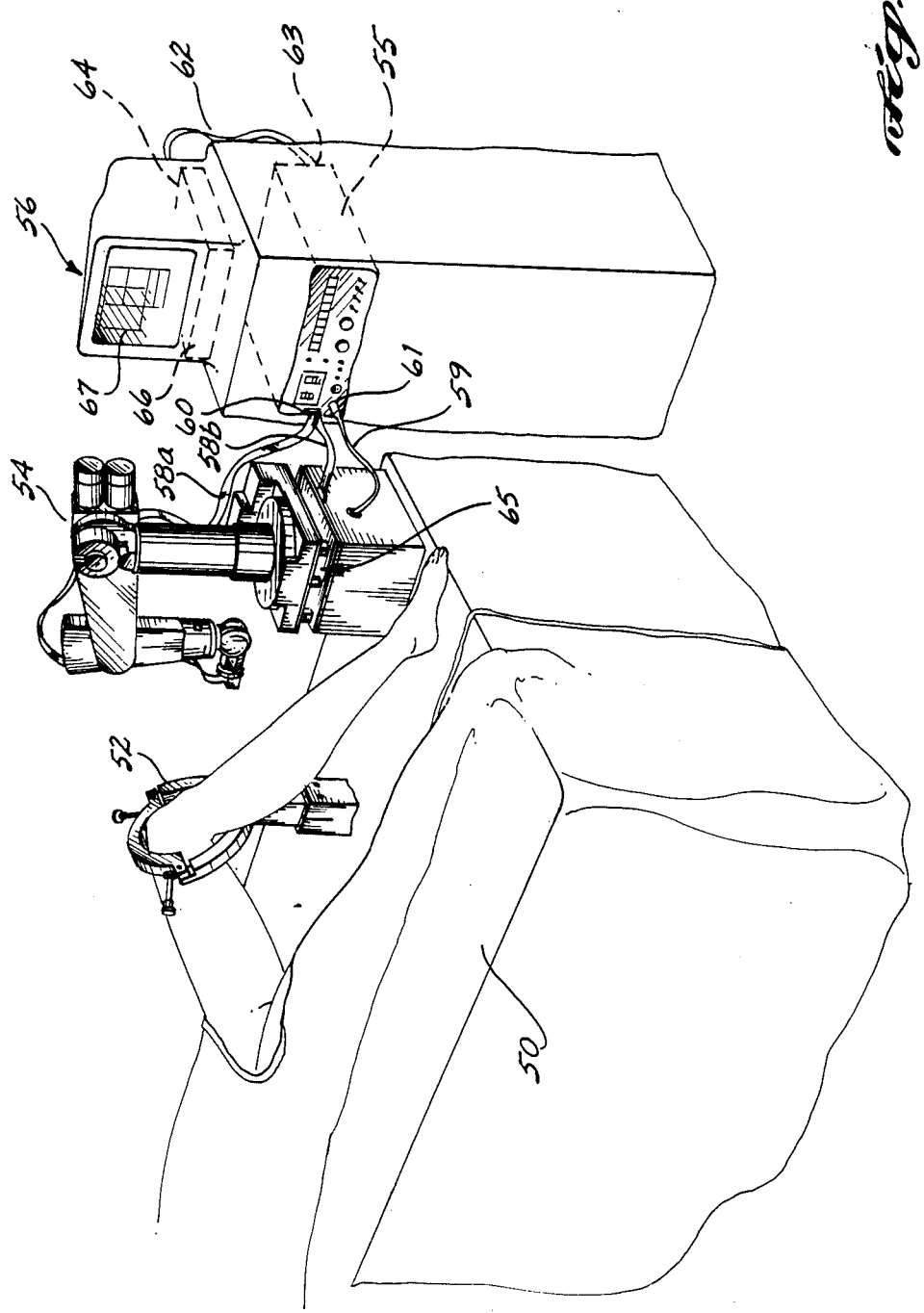
FIG. 3 is a pictorial view of the system of the present invention including a patient positioned on an operating table.

With reference to FIG. 3, one preferred embodiment of the system of the present invention utilizes an operating table 50, a bone immobilization device 52, a robot 54, a robot controller 55, and a robot supervisor 56. The patient is positioned so that the femur is supported and rigidly secured within the bone immobilizer. In practice, proximal femur displacement is prevented by placing sandbags or a secure belt over the hips of the patient. The immobilizer is attached to the operating table by the immobilizer base, not shown. Thus, throughout the TKA, the femur position is fixed in relation to the operating table 50.

The robot is rigidly attached to the operating table 50 by robot safety stand 65. The operating table thus provides a reference structure for the positional relationship between the femur and the robot. In a preferred embodiment, a tool attached to a robot mounting flange that extends from the robot manipulator can be moved relative to the base, in any of the six degrees of freedom. With this system configuration, a tool connected to the mounting flange can be accurately positioned about the immobilized femur. The robot includes position-sensing means for generating signals indicative of the position of the mounting flange relative to a world coordinate system fixed with respect to the robot base.

The robot controller 55 directly controls and monitors the movement of the robot. The robot and its peripherals are connected to the controller by input/output cables 58a and 58b, and communications cable 59. The input/output cables 58 and communications cable 59 are connected to input/output port 60 and communications port 61, respectively. Movement commands are generated by the controller and sent to the robot via communications cable 59. Mounting flange position signals are received from the robot over communications cable 59, and processed by the controller. Monitoring and control of robot peripherals, such as the safety stand, are also carried out by the controller. Such peripherals are connected to the controller by input/output cables 58 via input/output port 60.

In one preferred embodiment, the robot supervisor 56 supervises the communications between the robot and the controller. The supervisor in the illustrated embodiment includes a personal computer (PC) 66 (shown in reference) and display device 67. The PC houses the robot supervisory programs and the system data. The supervisor may enhance the operation of the system by providing a simplified operator interface. The surgeon can then control the system without having to understand the robot command language utilized by the controller. The controller is connected to the supervisor by communications cable 62 that extends between the controller's supervisor port 63 and the supervisor's communication port 64 (both shown in reference). The robot controller and supervisor can be covered with a sterilized shroud during the operation and still be easily manipulated.

As noted above, the TKA is divided into two steps. In the first step, the desired spatial relationship between the prosthesis and the distal end of the femur is established. In one preferred embodiment, this step is accomplished by means of a prosthesis template that is attached to the robot mounting flange. Generally, the template includes a feature, such as a surface, a bore or a pointing member, that can be used to represent a task position that is relevant to the performance of a bone alteration task. For replacing the distal end of the femur with a prosthesis, the template feature preferably comprises a surface that corresponds to an outer surface of the prosthesis. When the template feature is placed in a desired position relative to the desired position of the prosthesis surface, then the template position, termed the reference position, is stored in the system database. In one preferred embodiment, the surgeon manually positions the template near the femur. Once the template position is correct, the robot arm is locked and the position of the template in the world coordinate system is recorded.

The second step of the TKA comprises the bone alteration tasks of cutting and drilling the femur in preparation for the prosthesis. In these tasks, surface cuts will be made by a surgical saw, and stud bores will be drilled by a surgical drill bit. The supervisory program combines the reference position with a geometric database to generate coordinate data for each cutting and drilling task. The geometric database describes the planes and axes in which the saw guides and drill guides, respectively, must be aligned to perform the specified bone alterations. A program is generated to command the robot to move the tool attached to the mounting flange to the proper position so that the tool is in place for the specific task. Once the tool is positioned, the robot arm holds the tool while the surgeon carries out the sawing or drilling task.

After the bone is prepared, the prosthesis is placed on the bone end. Because of the geometric exactness provided by the robot system, bone cuts and bores are achieved that allow for an accurate press-fit of the prosthesis onto the bone end.

Figure 4:
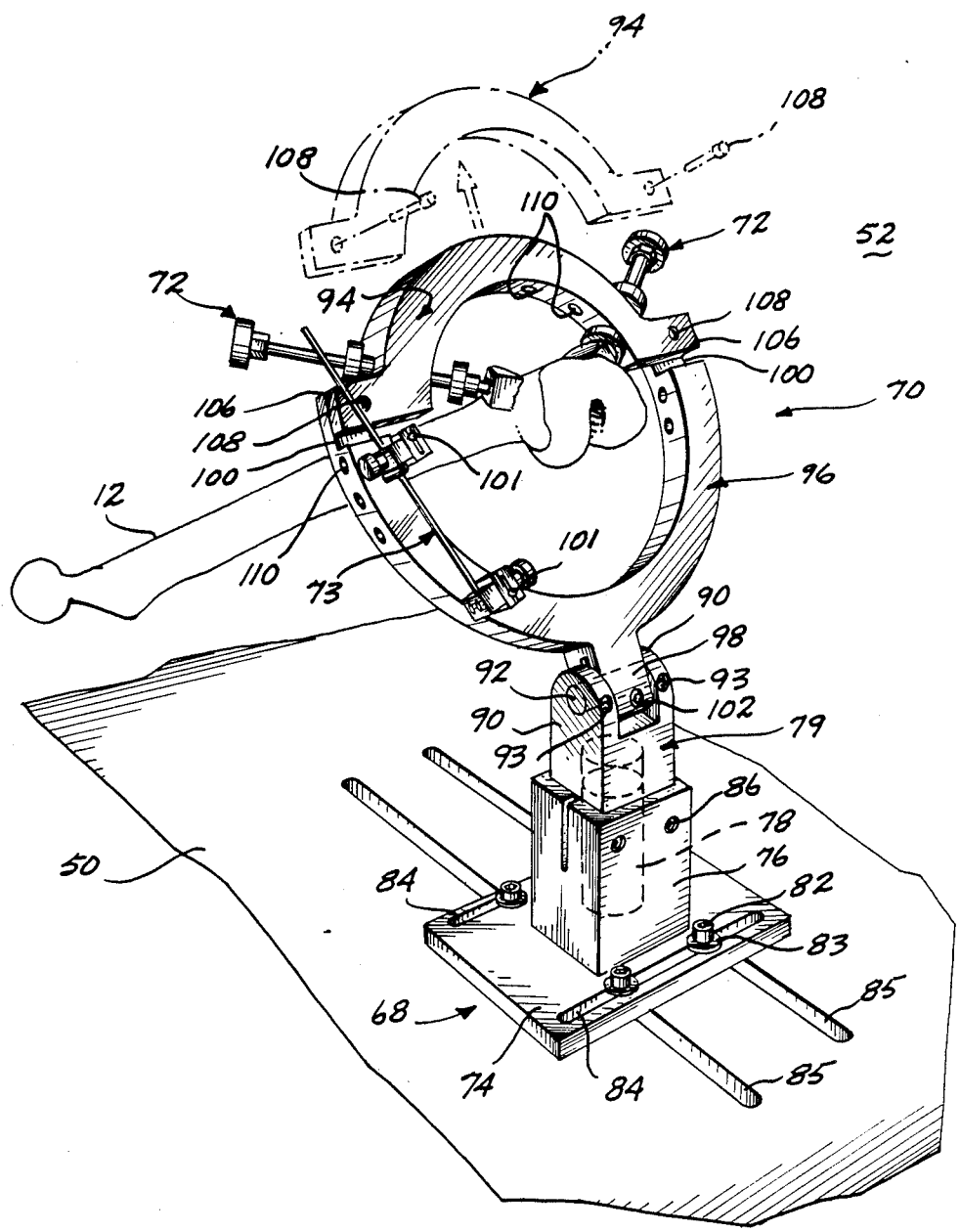
FIG. 4 is an isometric view of the bone immobilization device of the present invention with a representative femur suspended by the device.

Referring now to FIG. 4, one preferred immobilizer to be used with the present system includes base 68, bone-positioning frame 70, and bone fixation components 72. In one preferred embodiment, a tool-stabilizing device 73 is attached to the immobilizer. The stabilizing device will be discussed below. Although the full femur is shown, in an actual procedure, only a small portion of the distal end of the femur would be exposed.

The tibia, kneecap, ankle, etc., would be beside or below the femur in the foreground of FIG. 4.

The immobilizer base 68 connects the immobilizer to the operating table 50. The base includes sliding plate 74, base clamp 76, upright 78 (shown in reference) and upright clamp 79. The sliding plate includes bolts 82 and washers 83 to secure the plate onto the operating table. The bolts extend through channels 84 and threaded table runs 85. The immobilizer position can thus be adjusted relative to the table, both side to side and end to end. The position is secured by tightening the bolts 82 in the runs 85.

The base clamp 76 is hollowed to slidably receive upright 78. The height and rotational position of the immobilizer is adjusted by loosening screws 86 in the base clamp, thereby loosening the grip of the clamp on upright 78. Once the upright is adjusted to the desired position, the screws are tightened, thereby compressing the base clamp against the upright in secured relationship.

The upright 78 is preferably an integral part of the upright clamp 79. The upright clamp extends vertically as clamp flanges 90. Attachment cylinder 92 extends through and between the clamp flanges. Set screws 93 are positioned in the flanges normal to the attachment cylinder. The rotational position of the attachment cylinder is secured by tightening the set screws 93 into the flanges and against the attachment cylinder.

The bone-positioning frame 70 is made up of semicircular upper frame 94 and lower frame 96. Lower frame 96 includes frame tab 98, connecting ledges 100, and anchor pins 101 (discussed below). The frame tab 98 extends centrally from the lower frame. A bore runs through the frame tab and is shown in reference. The frame tab is split from the bore to the bottom of the tab. Bolt 102 connects the lower portions of the split tab and can be tightened to reduce the bore diameter. The frame tab is coupled to the frame clamp by attachment cylinder 92 which extends through the tab bore. The angle of the frame relative to the base plate is adjustable by rotating the frame over the attachment cylinder. Once the desired frame angle is achieved, bolt 102 is tightened to secure the tab against the attachment cylinder. Thus, the angle of the frame is adjusted by loosening either the bolt 102 or the pair of set screws 93, to allow the frame or the attachment cylinder, respectively, to rotate.

The upper frame 94 includes projections 106. The upper frame is connected to the lower frame by the securing of projections 106 to the ledges 100 by screws 108. The upper frame is thus readily removable from the lower frame for ease of positioning the bone within or removing the bone from the immobilizer.

The frame includes a plurality of threaded radial bores 110 spaced along the frame edge. The fixation components 72 of the immobilizer extend through the bores. Once the bone is positioned through the frame, and the knee joint exposed, the fixation components are tightened to the femur and to the frame edge to hold the femur in place.

It is preferable to grip the exposed bone rather than the skin or other tissue. Since the posterior portion of the knee is not generally widely exposed, the fixation components will typically be situated in the upper portion of the frame so as to be in a position to contact the exposed anterior portion of the femur. Thus, the majority of the bores 110 are positioned in the upper area of the frame. Alternatively, if other bones are being operated on, it may be preferable to have the fixation components enter the bone from the posterior side. In such a case, the frame bores 110 are positioned about the lower frame 96. Additionally, if the fixation components are both positioned through the upper frame or both through the lower frame, then the upper frame can be removed from the lower frame while the bone remains secured to one half of the frame by the fixation components.

Figure 5:
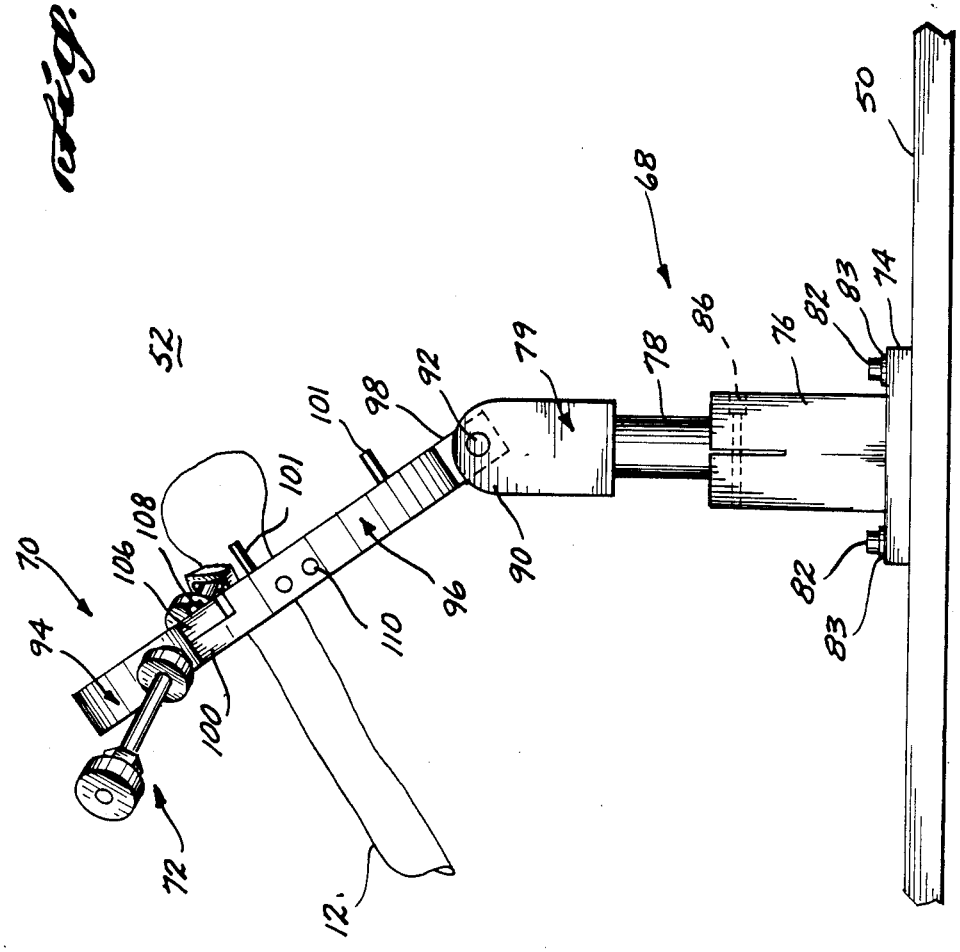
FIG. 5 is a side view of the bone immobilization device with the frame and fixation components shown adjusted to a raised position relative to the base of the device.

As shown in FIG. 5, the bores 110 through the frame do not lie within the plane of the frame, but are set at an angle. The angling of the bores allows the fixation components to extend back and away from the area of the operation, thereby allowing maximum access to the bone. In this manner, the end of the femur is approachable by the surgeon from almost any angle and complete surface cuts can be made without repositioning any part of the immobilizer.

The immobilizer provides six degrees of freedom for positioning the bone. Translational freedom is provided by adjusting the sliding plate along the channels 84, and runs 85, and by adjusting the height of upright 78 within base clamp 76. Rotational adjustments are provided by rotation of the upright 78 within base clamp 76, rotation of the frame 70 about attachment cylinder 92, and rotation of the fixation components about the frame 70; i.e., by repositioning the fixation components relative to the frame by using a number of bores 110.

Figure 6:
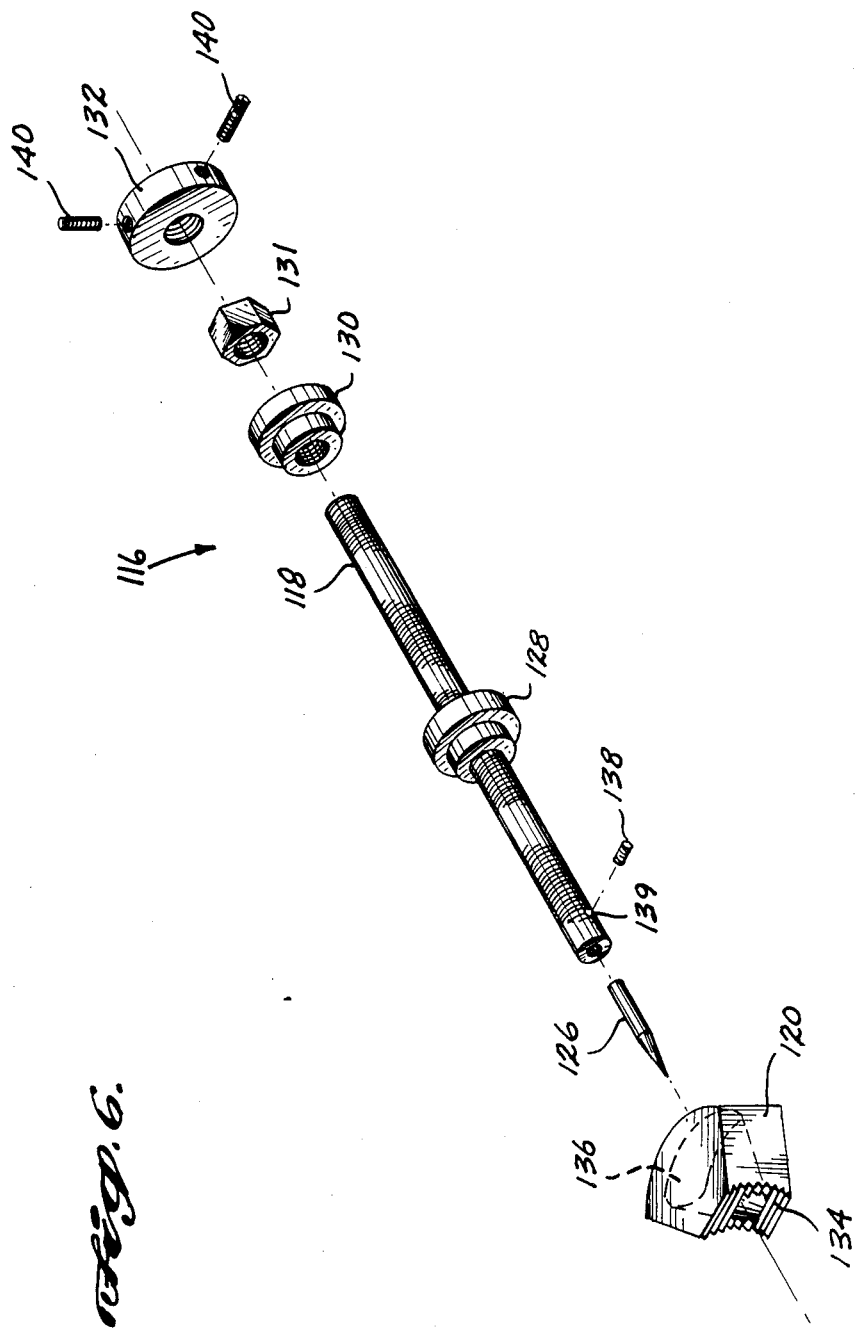
FIG. 6 is an exploded view of one fixation component of the bone immobilization device.

With reference to FIG. 6, one preferred fixation component is a coacting grip 116. A pair of grips are adequate to rigidly secure a bone within the bone immobilization device. Each coacting grip 116 includes a threaded shaft 118, a contact washer 120, a point 126, a washer nut 128, a frame nut 130, screw nut 131, and a screw head 132. The contact washer is preferably wedge shaped and has a serrated contact surface 134. A shaft bore 136 extends through the contact washer, relatively normal to the contact surface. The bore is oversized so that the angular relationship between the contact surface and the shaft is adjustable by rocking the washer about the shaft. In one preferred embodiment, a variety of contact washers are available, the washers being differentiated by the contours of their respective contact surfaces. The contact surfaces range from a flat surface to a concave surface. The specific contact washer for each coacting grip is chosen during the operation so that the contact surface closely conforms to the bone surface against which the washer will be tightened.

The point 126 is attached to the shaft by set screw 138 inserted through bore 139 against the point. Alternatively, the point 126 may be an integral part of the shaft.

In use, the pointed shaft 118 is threaded through a bore 110 in the frame. The portion of the shaft in the interior of the frame is threaded with the washer nut 128 and extended through the contact washer 120. The shaft position is adjusted until the point 126 slightly penetrates the bone. On the outside of the frame, the frame nut 130 is then screwed onto the shaft and tight against the frame to secure the shaft relative to the frame. The contact washer 120 is then adjusted about the shaft so that the contact surface 134 contacts as much bone surface as possible. The washer nut 128 is then tightened down to hold the contact element in contact with the bone. The teeth of the serrated contact surface slightly penetrate the bone to prevent slippage. The screw head, screwed against screw nut 131 and attached by set screws 140 to the shaft, provides a gripping surface to be used in the shaft-adjusting process. The tightening of the two coacting grips generally takes place simultaneously.

The coacting grips 116 are capable of suspending the femur without support from below. The suspension is achieved by the coacting forces of the shaft points and contact washers. Each shaft point provides a force against the bone that prevents the bone from moving in directions perpendicular to the axis of the shaft. Each contact washer provides a surface force against the bone that prevents the bone from moving in directions parallel to the shaft. This two-point suspension method reduces interference with the femur end as well as damage to the bone.

The immobilizer 52 can be used in a variety of operations where it is desirable to rigidly immobilize a bone throughout a procedure. Once the bone is immobilized, the operation can proceed. The next step of the present invention is to teach the robot the desired position of the bone alteration task.

Figure 7:
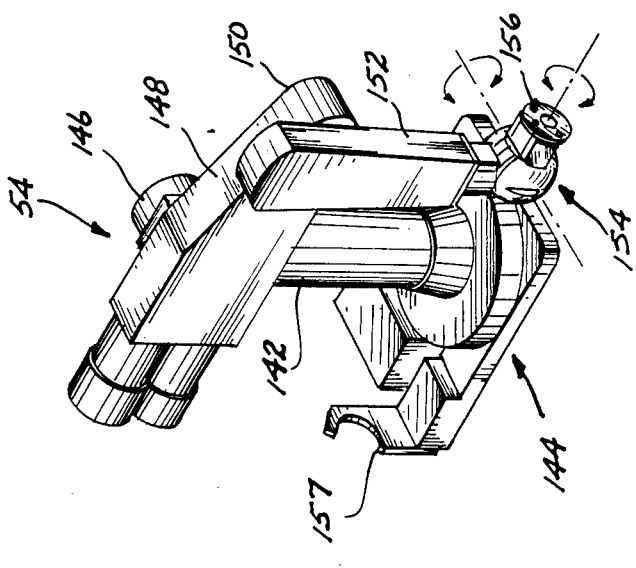
FIG. 7 is an isometric view of a robot used in the system illustrated in FIG. 3.

Desirable characteristics of a robot used in the present system include that the robot be capable of moving a tool mounted to the robot in six degrees of freedom; that the mounting flange be capable of gripping or adaptable to grip a variety of surgical tools; that the robot has a high repeatability of mounting flange positioning; and that certain safety features be available on, or integratable into, the robot and control system. With reference to FIG. 7, one suitable robot 54 is the PUMA 200 robot available commercially through Unimation. The PUMA 200 robot is relatively small, and thus will fit readily into a surgical area and can be mounted directly onto or adjacent an operating table. The robot is rigidly mounted in relation to the immobilizer device by securing the robot directly to the operating table or to a safety stand 62 which, in turn, is mounted on the operating table.

The robot 54 includes a trunk 142 extending from a base 144, a shoulder 146 connecting the trunk to an upper arm 148, an elbow 150 connecting the upper arm to a lower arm 152, and a wrist 154, attached to the lower arm, from which extends a mounting flange 156. The section of the robot that includes movable parts is referred to as the manipulator. The manipulator includes permanent-magnet DC servomotors for driving the robot movement. Incremental optical encoders for determining manipulator position relative to a fixed point on the base robot, and for determining manipulator velocity, are included in the joints. The encoders convert positional data into electrical signals. Generally, the position of each section of the manipulator is combined to determine the position of the mounting flange or a tool attached to the mounting flange. When the robot is not in use, the wrist rests in nest 157.

Figure 8:
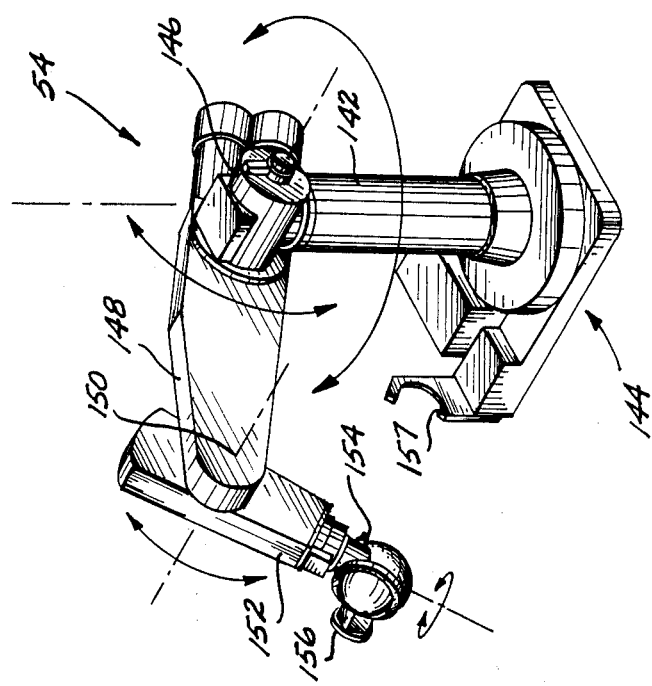
FIG. 8 is an isometric view of the robot illustrated in FIG. 7 showing the movement capabilities of the robot.

With reference to FIG. 8 in conjunction with FIG. 7, the manipulator is capable of moving the mounting flange 56 in six degrees of freedom. The robot rotates about the vertical trunk. The upper arm is raised and lowered by rotation about the shoulder. The lower arm raises and lowers the wrist by rotation around the elbow. Finally, the wrist rotates about three axes defined by the longitudinal axis of the lower arm, the wrist, and the center of the mounting flange.

Attachments to the mounting flange, such as mechanical grippers or electronic sensing devices, are available from the robot manufacturer or from other manufacturers specializing in such attachments. With reference to FIG. 9, the standard mounting flange provided on the PUMA 200 robot has screw holes 158 positioned about the perimeter of the flange. The flange also includes an alignment pin 159 that is used to ensure repeatable positioning of tools on the flange. The present system utilizes a coupler 160 that connects to the mounting flange 156 and couples various tools to the robot wrist. The coupler includes connecting plate 162, coupling block 164, identification component 166, signal port 168, connecting bore 170, and alignment studs 172. The connecting plate alignment bore (not shown) is positioned so as to match with the mounting flange alignment pin 159. The plate is secured to the mounting flange by screws 173 extending through plate bores 174 to screw holes 158. The coupler is fixed on the mounting flange for the duration of the surgery. In this manner, the position of the coupler components are fixed relative to the robot mounting flange.

The coupling block 164 is perpendicular to and offset on the connecting plate. Tools are attached directly to the coupling block during the operation. Each tool has an attachment flange, an example of which is shown in FIG. 10, that mates with the coupling block. The flange 175 includes a thumbscrew 176 that extends through the flange into the connecting bore 170. The flange also includes a pair of bores 178 that mate with the alignment studs 172. Each tool includes a similar attachment flange and is precisely and repeatably mountable on the coupling block. The position of each tool relative to the position of the mounting flange is thus known when the tool is mounted. This repeatable mounting capability allows the robot to be taught the mounted-tool configuration in a simple manner.

It is standard practice in robotics to direct robot movements in terms of tool positions. This is done by first teaching the robot a tool definition. A tool mounted on the mounting flange is described to the robot as a single point that is offset from and oriented relative to the robot mounting flange. A common point used for defining a tool is the tip of the tool or some similar point remote from the attachment flange. A common robot control function accepts an array of values that defines the tool point relative to the mounting flange. Tool positioning commands can then be utilized. The robot control functions include implicit transformations from a tool position in a coordinate system to a robot mounting flange position. Given a movement command, the robot will move the robot mounting flange so that the tool point is at the commanded position.

The efficiency of the present system is increased by the inclusion of an identification component 166 on the coupling block. This component is used to identify the tool attached to the robot. This identification is then compared to an identification code stored in the control memory that corresponds to the tool required for the task at hand. For example, the identification code for the saw guide will satisfy the tool identification test that is run during the bone-cutting steps of the procedure. The identification component is used as a safeguard against the attachment of an incorrect tool. Additionally, it is a time-saving device in that the robot controller indicates to the surgeon immediately that an improper attachment has taken place so that time is not wasted in identifying a tool attachment error and correcting it during the operation.

In one preferred embodiment, the identification component is comprised of five phototransistors 180 arranged in a pattern along the surface of the coupling block. Each phototransistor is an emitter and receiver pair and is capable of transmitting and receiving an infrared signal. Each phototransistor is connected to the signal port 168 by a wire (not shown) suitable for carrying a signal. Signal port 168 is connected to the controller by input/output cable 58a. Radiation emitted from each phototransistor is detected by the respective receiver if it is reflected back; i.e., if a surface is positioned slightly above the sensor to thereby cause the light to reflect back. If no surface is present, or one lies flush against the sensor, then no reflected light is detected. Thus, the signals sent by the phototransistors to the controller might be interpreted digitally as 1's and 0's for reflected and nonreflected signals, respectively. The output of the sensors is collectively read as a binary word. Thus, 32 different identification codes are represented by the five sensors. The corresponding tool attachment flange surfaces are patterned with slight bores. One pattern corresponds to each tool. On the sample flange 175 the identification pattern 181 will be flush against the phototransistors on the coupling block when the flange is attached. The pattern 181 includes three areas that are slightly bored so as to provide a means for reflecting light emitted from the phototransistor back onto the coupling block. No light will be reflected from the other two phototransistors because the attachment flange will be flush against the phototransistors. Thus, the identification for the tool corresponding to the sample attachment flange is some combination of three 1's and two 0's, the combination depending upon the order in which the signals are read. During the TKA, a continuous signal is passed between the controller and the phototransistors. The return signal is read by the controller at the tool mounting step and the identification code determined by the control program.

With reference to FIG. 11, the robot safety stand 65 includes top plate 182, base plate 183, support legs 184, and spring assemblies 185. The base 144 of the robot is secured to the top plate 182 by screws 186. The base plate in turn is secured to the operating table 50 by screws 187. In this manner, the robot position is stable relative to the operating table.

Although the robot is preferably programmed to move slowly, so that there is little chance of an accident occurring due to the robot striking an object at a high speed, there is still a chance that the robot may encounter a rigid object while it is moving. If such an incident occurs, power to the manipulator should be cut off immediately. In one preferred embodiment, the force of the robot against a rigid object will cause the top plate to tilt away from the base plate. The compliance of the stand prevents the robot from damaging the object and provides an indication to the controller over cable 58b that the power should be automatically shut off. Since the PUMA 200 robot is relatively lightweight, a great deal of force need not be applied by the robot to a rigid object in order for this power-down situation to occur.

As illustrated in FIG. 12, a support leg includes upright 188 and ball bearing 189. The ball bearing is captured between the upper portion of the upright and lower side of the top plate which is slightly indented to receive the ball bearing. Adjacent each upright is a contact switch 190 attached to the lower side of the top plate. The upright and contact switch are made of electrically conductive materials and form a simple ground loop detection circuit. The contact switch is positioned so that when the top plate rests on the ball bearing and upright, the contact switch completes the circuit. Each upright is connected to a wire, not shown, and the wires are bundled into cable 58b and connected to the robot controller input/output port 60. During periods of robot movement, the controller continuously polls the circuits to check for a break in the continuity between a switch and an upright. When this occurs, power to the robot is immediately shut off.

Each spring assembly 185 includes a spring 193, a casing 194, and a spring mount 195. The spring mount extends downwardly from the lower side of the top plate and includes a securing flange 196 on the unconnected end. The spring wraps around the spring mount and is secured on the mount by securing flange 196. The spring and mount are encased in casing 194 which is hollow and extends upwardly from the upper side of the base plate. When the top plate rests on the support legs, the springs are slightly compressed within the casings, thereby providing a downward force against the top plate and an upward force against the base plate. In this manner, a firm base is established for the robot.

With reference to FIG. 13, the support legs and spring assemblies are positioned between the plates so that the tilting of the top plate in any direction will result in at least one contact switch losing contact with an upright. When the top plate is tilted, the spring mount in the spring assembly, or assemblies, attached to the portion of the top plate tilting away from the base plate will slide upwardly and away from the casing by a compression of the spring. In this manner, the plates continue to be connected by the spring assemblies so that the robot does not topple from the stand.

Figure 14:
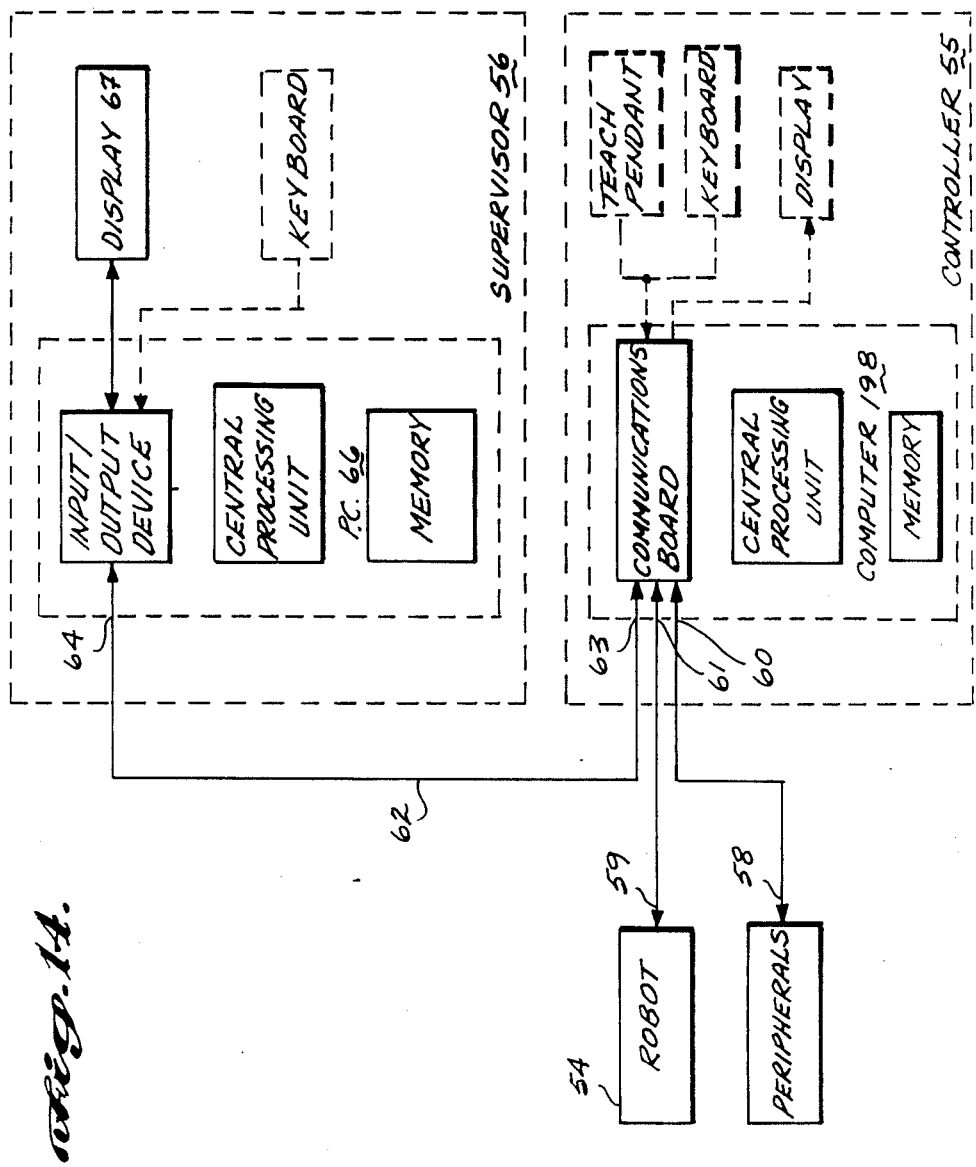
FIG. 14 is a block diagram of the robot and peripherals, controller, and supervisor of the system of the present invention.

Referring now to FIG. 14, the robot is controlled by controller 55 that is available through the robot manufacturer. The PUMA 200 controller includes a Digital Equipment Company (DEC) LSI-11 computer 198 which includes a processor, memory, and communications board. The communications board includes robot-communications port 61, input/output port 60, and supervisor port 63. The robot is also provided with a teach pendant, an input device, such as a keyboard, and a display device, such as a terminal display screen, all shown in reference.

In the PUMA 200 controller, the control programs are stored in a Complementary Metal Oxide Semiconductor NCMOS) nonvolatile memory. The robot commands and feedback are routed through the robot-communications port 61. The input/output port 60 is a programmable control output that is actuated by the control programs. A variety of peripherals, such as the safety stand and tool identification device can be attached through the input/output port.

The PUMA controller is provided by the manufacturer with its own operating system/robot control language known as VAL-II (Versatile Assembly Language). Programs are written in VAL-II to control the movement of the robot. The programs include: robot-control programs for directly controlling the robot with motion instructions; process-control programs that run parallel to the robot control programs for monitoring and controlling external processes via lines connected to the input/output port; and system programs for system operation. The programs are stored in the controller memory and processed by the controller. A sampling of the VAL-II commands and functions used by the present system to implement robot movements is listed in TABLE I.

TABLE I

| Name | Description |
| --- | --- |
| MOVE <location> | Moves the robot to the position and orientation described by "location." |
| SET <location variable> = <location variable> | Sets the left variable equal to the right variable. |
| HERE <location variable> | Sets the value of a transformation or precision point equal to the current robot location. |
| TOOL { <compound> } | Sets the value or definition of the tool transformation equal to the transformation value given. |
| SPEED (<expresssion>) | Returns one of the speed values used by the system. The value is always a percentage of "normal" speed; i.e., SPEED 100. |
| APPRO <location>, <distance> | Moves the tool to the position and orientation described by "location," but offset along the tool Z-axis by the distance given. |
| DISTANCE (<compound, compound>) | Returns the distance in mm between the points defined by the two specified transformation values. |
| NEST | Moves the robot into its nest. |

There are several methods for controlling the movements of the robot. The robot is equipped by the manufacturer with a teach pendant (not shown) that can be connected to the input/output port 60 of the controller. The teach pendant is a hand-held device for interactively maneuvering the robot. The teach pendant is generally used to maneuver the robot through a series of steps making up a path. The controller records points along the path so that the robot can then repeat the steps under the controller's guidance. A joystick, voice control device, or other movement indicator provide suitable methods for controlling robot movement interactively. These methods are contrasted with the method wherein the controller processes a program written in VAL-II that is stored in the controller memory or passed from a supervisor. As the VAL-II program is run, the robot moves through the programmed steps. The robot can also be placed in a passive mode wherein the manipulator is manually moved; i.e., by an operator actually grasping and moving the manipulator through a recordable path. In this mode, the servomotors are disabled while the encoders remain active. All of the other modes are referred to as active modes. In these modes, both the servo motors and encoders remain active.

The robot is capable of recognizing and operating within two coordinate systems: a world coordinate system and a tool coordinate system. In the world coordinate system, the origin of the system is at the shoulder or some other point of the robot which remains fixed relative to the base. In the present system, the origin is fixed relative to the operating table and to the patient's bone. The robot can be programmed to move an attached tool to any world coordinate position.

In the tool coordinate system, the origin defaults to a point on the robot mounting flange that moves with the flange. The default origin can be replaced by an origin related to, and more useful for, a specific tool attached to the flange. The tool coordinate system moves with the mounting flange as it is moved by the robot. Each tool can be defined by tool data points in the tool coordinate system. As described in greater detail below, the data representing a tool definition is combined with the template reference position and with a geometric database describing the prosthesis to determine the position of the tool, e.g., a saw guide, for each task.

The robot controller has a supervisor port into which a supervisor can be connected. Information describing and aiding in the implementation of the supervisory-communications interface is provided with the controller by the robot manufacturer. The supervisor 56 may include a personal computer (PC) 66 and a display device 67. The PC includes a central processing unit (CPU), input/output ports, and memory. In one preferred embodiment, a PCs Limited 386, an IBM-compatible personal computer manufactured by Dell Computer Corporation, connected to a color-display device, is used as the supervisory system. The PC is connected to the controller's supervisor port 63 through the PC's COM2: serial port via cable 62. Through this connection, programs run on the PC supervise the robot controller. The supervisor provides data as well as control commands and programs in the VAL-II language. Although a supervisor is used, all robot movement commands are preferably routed through the controller to the robot.

A touch-screen input system is used so that the monitor and the input device are integrated. Personal Touch Corporation's Electronic Input Screen, available under the trademark TouchWindow, is fixed to the front of the display device and used as the command input device during the operation. Such an input screen is highly desirable in a surgical environment in that it can be draped with a transparent sterilized shroud and still be easily manipulated by the surgeon. The bone alteration control program provides large squares displayed on the monitor that correspond to specific commands. The screen area immediately in front of the display square corresponding to the desired command is simply touched by the surgeon to indicate the command choice. The use of the touch-screen input system eliminates the need for other input and display devices, such as the teach pendant and keyboards, during the TKA. However, during system programming and data entry, either the supervisor or controller keyboard is used to input information.

While, in one embodiment of the system of the present invention, the TKA program is implemented using only the controller, the addition of the supervisor in an alternative embodiment increases the capabilities of the overall system. For ease of description, the system will be described with the supervisor acting as the main processor. However, it is understood that in alternative embodiments, the controller is used to perform additional or all processing functions.

By using the supervisor, a programming language that is more specific to bone alteration surgeries, and easier to implement than the VAL-II language, is implemented. Preferably, a high-level English-like language is used so as to increase the ease of using the system by those who are familiar with such surgeries, but may not be familiar with the VAL-II language or computer programming in general. Existing languages, such as BASIC, can be used, or others can be developed for the specific purpose. Any program downloaded from the supervisor to the controller is written in the VAL-II language so that the controller can process the program and generate movement commands.

In the present system, the high-level language program generates a VAL-II program. The VAL-II program calls a library of VAL-II sub-programs. The sub-programs, in turn, call a set of VAL-II primitives. It is the set of primitives that command the robot movements. The use of a high-level language to write the robot control programs in VAL-II is analogous to using a high-level language to generate an assembly language. In the latter instance, a program written in the high-level language, such as BASIC or C, is compiled to create a meta-code. The meta-code is linked to a function library to include the functions referenced by the program into the meta-code. A second linking operation is performed to create the assembly language program. These steps are common in the area of programming with high-level languages.

By establishing a program in a high-level language, the program can be tailored to the application. In the present system, the program for the bone alteration surgical procedure is directed to template positioning, and bone cutting and boring. Thus, the high level language only references those VAL-II programs that are necessary to perform these tasks. Preferably, simple operator commands, such as "DO DISTAL CUT," generate, through the process described above, the VAL-II primitives directing the movement of the robot to carry out the task. The surgeon is spared from making any more detailed programming decisions when a high-level language is used. A skeleton of a sample custom surgical task description language will be used in the present description as an illustration.

Two tasks must be carried out prior to using the robot system: establishing a descriptive geometric database for the prosthesis preparation task; and developing programs in VAL-II and a high-level language that describe and direct the procedures. In one preferred embodiment, geometric databases are established that describe, for each prosthesis, the geometric relationships between the prosthesis and the bone-cut planes and bore axes necessary to prepare the bone for the prosthesis. Preferably, to establish the database, a program is run to: accept a high-level language scrip describing the geometry of a prosthesis interior surface; check the geometry for consistency; and produce a machine-readable database file for use by other programs. The database program utilizes geometric primitives that are recognized by the VAL-II language. The geometric primitives are the basis for the robot-movement commands. The primitives are established as POINT—consisting of a triplet (x, y, z) or a name;
LINE—consisting of two points, or a name;
EDGE—which is a line bound to a plane;
PLANE—consisting of two or more lines; and
TEMPLATE—consisting of planes, lines, and points.

Using these primitives, a line can be defined by two points, and a plane can be defined by two lines. The template is defined by the five planes: anterior, posterior, distal, and two chamfer; and the two lines for the medial and lateral bores. For each plane, one line is specified as the APPROACH EDGE so that the robot will move a tool to the plane from a specific position and orientation within that plane. The geometric primitives can be defined in terms of other primitives referenced by name, with the exception of a template that is self-contained. Using the structured prosthesis definition, two prosthesis geometries that are related and differ only in scale can be defined by the same script by changing only the lowest level, point (x, y, z), definitions to suit the different sized component. The geometries are described in a coordinate system wherein the origin is some fixed point on the template. When the template is actually used to determine the desired prosthesis position, and its world coordinate position is established, all of the data in the geometric database can be transformed to represent points in the world coordinate system.

A database file is built for each prosthesis. A sample of a prosthesis data entry script is listed in Table II.

TABLE II

FILENAME; "Type A"    # Type A Task (prosthesis)

define free lines a through f to serve as plane boundaries
POINT end __1a OF LINE line __a IS −1.0, −1.0401, 1.7266
POINT end __2a OF LINE line __a IS 1.0, −1.0401, 1.7266
POINT end __1b OF LINE line __b IS −1.0, −.9898, .8561
POINT end __2b OF LINE line __b IS 1.0, −.9898, .8561
POINT end __1c OF LINE line __c IS −1.0, −.6000, 5089
POINT end __2c OF LINE line __c IS 1.0, −.6000, .5089
POINT end __1d OF LINE line __d IS −1.0, .6000, .5089
POINT end __2d OF LINE line __d IS 1.0, .6000, .5089
POINT end __1e OF LINE line __e IS −1.0, .8682, .7513
POINT end __2e OF LINE line __e IS 1.0, .8682, .7513
POINT end __1f OF LINE line __f IS −1.0, .8883, 1.0211
POINT end __2f OF LINE line __f IS 1.0, .8883, 1.0211
now define the planes
EDGE proximal __edge OF PLANE anterior __plane
IS LINE line __a
EDGE distal __edge OF PLANE anterior __plane
IS LINE line __b
EDGE anterior __edge OF PLANE anterior __chamfer __plane
IS EDGE distal __edge OF PLANE anterior __plane
EDGE posterior __edge OF PLANE anterior __chamfer __plane
IS LINE line __c
EDGE anterior __edge OF PLANE distal __plane IS EDGE
posterior __edge OF PLANE anterior __chamfer __plane
EDGE posterior __edge OF PLANE distal __plane
IS LINE line __d
EDGE anterior __edge OF PLANE posterior __chamfer __plane
IS EDGE posterior __edge OF PLANE distal __plane
EDGE posterior __edge OF PLANE posterior __chamfer __plane
IS LINE line __e
EDGE distal __edge OF PLANE posterior __plane IS EDGE
posterior __edge OF PLANE posterior __chamfer __plane
EDGE proximal __edge OF PLANE posterior __plane
IS LINE line __f
now define two free lines for the bore axes
POINT top OF LINE hole __1 IS .8, 0, 0.508
POINT bottom OF LINE hole __1 IS .8, 0, 2
POINT top OF LINE hole __2 IS −.8, 0, 0.508
POINT bottom OF LINE hole __2 IS −.8, 0, 2

Each of these primitives is added to a list of template members. It is preferable to check the data by checking each point of each of the lines of the planes for coplanarity with all other constituent points of the plane, as well as linking of all

| TASK leg | # perform the task on a leg |
|---|---|
| DO select | # select a procedure |
| POSITION TEMPLATE leg | # position the template |
| DO cuts | # make the cuts |
| DO holes | # make the holes |

The sample task could control a right knee TKA. Each of the actions may reference one or more subtasks that will carry out the procedure. For example, in the "DO cuts" action, one of the subtasks would be to choose the cut to be made; i.e., distal, proximal, etc. When the action references a robot movement, the appropriate VAL-II programs are downloaded to the controller and executed. The remainder of the control system operation will be described after a discussion of the tools utilized in bone alteration surgeries.

Figure 15:
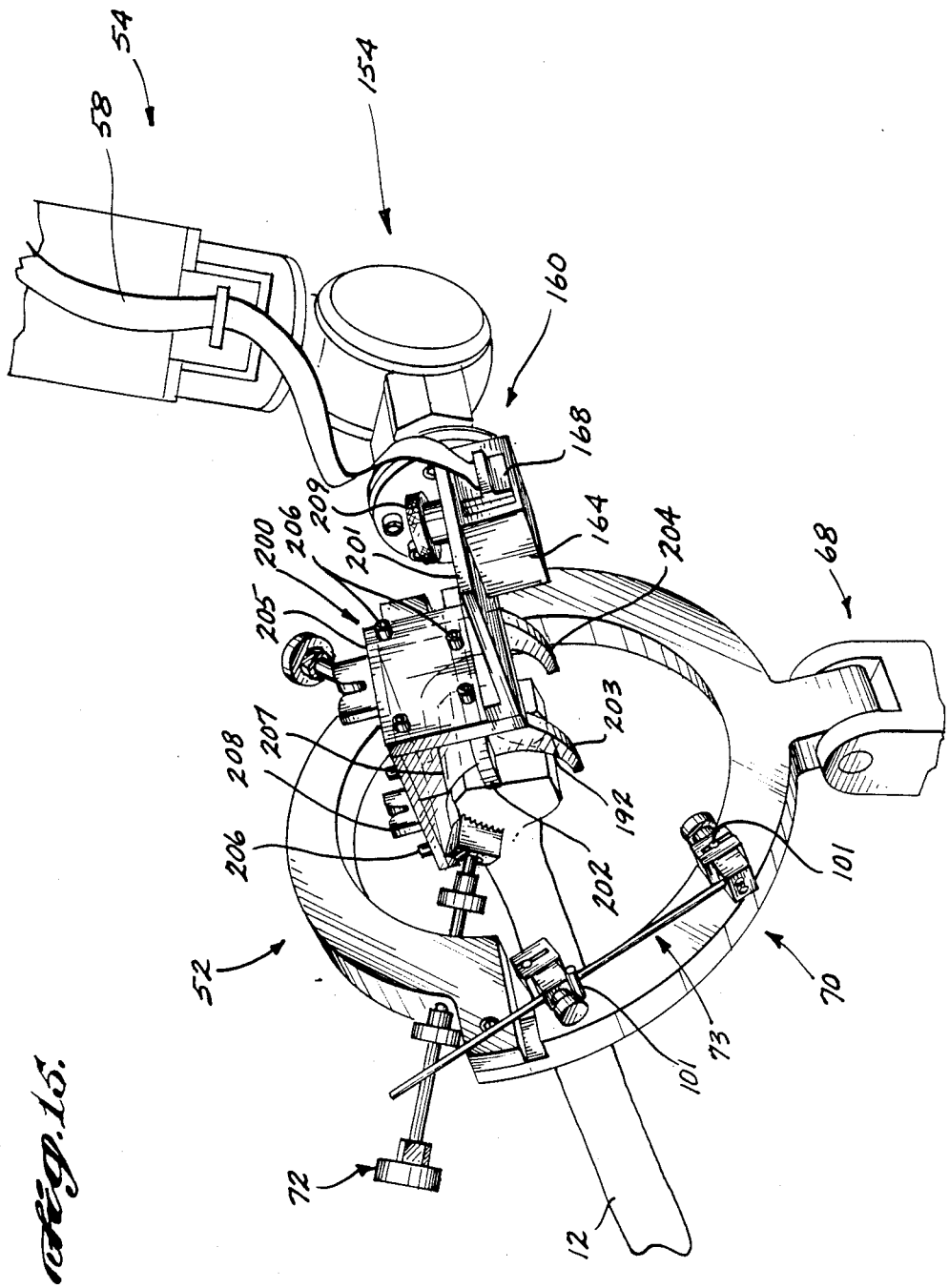
FIG. 15 is an isometric view of a use of the prosthesis template of the present invention attached to the robot and positioned near an immobilized bone.

Once the bone is immobilized, the position of the femur must be taught to the robot. A prosthesis template is used for this task. With reference to FIG. 15, the template 200 includes an attachment flange 201, a horizontal plate 202, two separated vertical plates 203 and 204, and a stabilizing plate 205. The plates are secured to one another by pins 206. In practice, the template is mounted to the coupler, and the robot mounting flange and the template are positioned adjacent the exposed femur end. A cut bone 12 is shown to illustrate the relationship between the template inner plate edges and the surface cuts. This relationship corresponds to the relationship between the prosthesis exterior and interior surfaces.

The template is constructed so that it generally fits over the existing femur anatomy. This is of particular value in situations where large amounts of the bone surface have been lost to disease or damage, since those situations greatly hinder visualization of the completed implant when using the conventional jig systems.

The template includes cut-guide marks 207 and rod-alignment tabs 208 to enhance the alignment and visualization processes. The cut-guide marks correspond to the anterior, distal and posterior planes that define the inner surface of the prosthesis. Thus, the surgeon can visualize whether there will be any problems with making adequate surface cuts in the bone to allow proper fitting of the prosthesis. For example, if a large notch is present in one condyle, the surgeon can mentally extend the distal cut-guide mark to determine whether, with a given cut plane, enough healthy bone is present to provide a loaded fit of the prosthesis.

The rod-alignment tabs 208 can be used to attach a straight rod above the center of the implied prosthesis position, and perpendicular to the distal cut plane. The tabs are extensions including slots that run parallel to the distal-proximal axis. The slots are dimensioned so that a conventional alignment rod can be set between them. By adjusting the template position, the rod can be aligned with the longitudinal axis of the femur.

Figure 16:
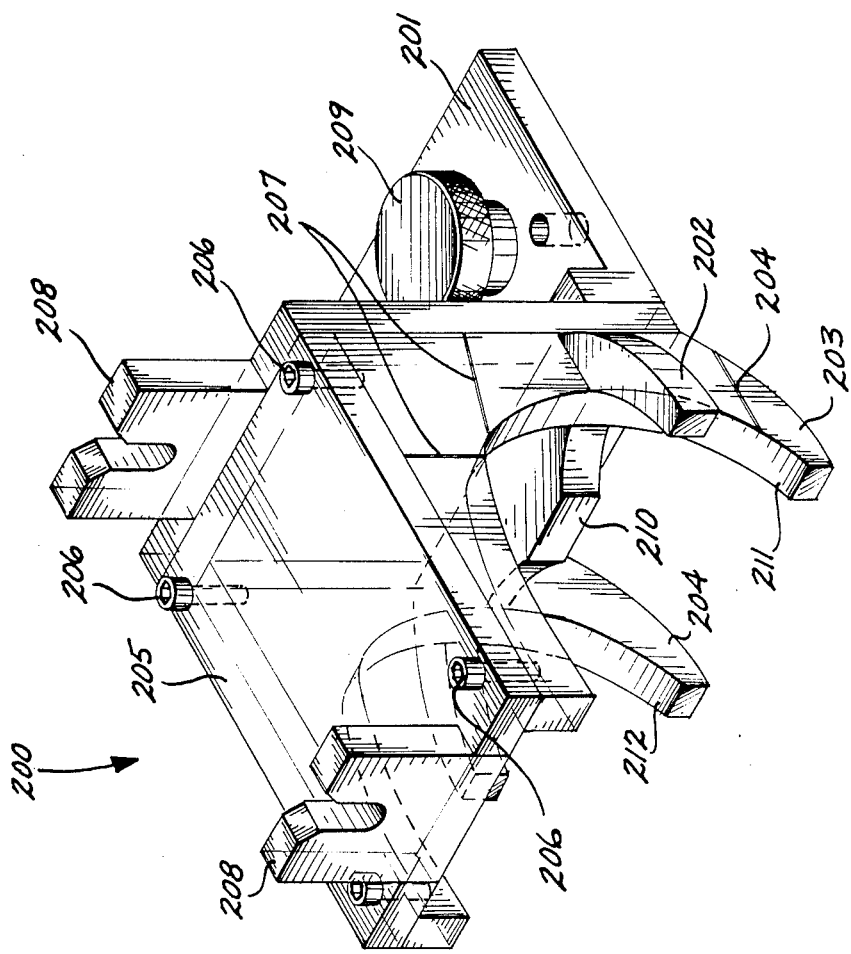
FIG. 16 is an isometric view of the template illustrated in FIG. 15.

With reference to FIG. 16, the inner edges 210–212 of the template create an inverse image or mold of the prosthesis exterior surface. Three contoured edges are adequate to define the major contours of the prosthesis exterior surface. Thus, the inner edges of the template correspond to the exterior portion of the prosthesis. Additional plates can be used to define the contours in greater detail provided the plates allow the surgeon to easily view the bone and the inner edges from a variety of angles.

The horizontal edge 210 has concave side edges corresponding to the condyles and a flattened convex central edge corresponding to the notch margin. The vertical edges 211 and 212 are concave and correspond to the anterior-to-posterior line of the condyles.

Figure 17:
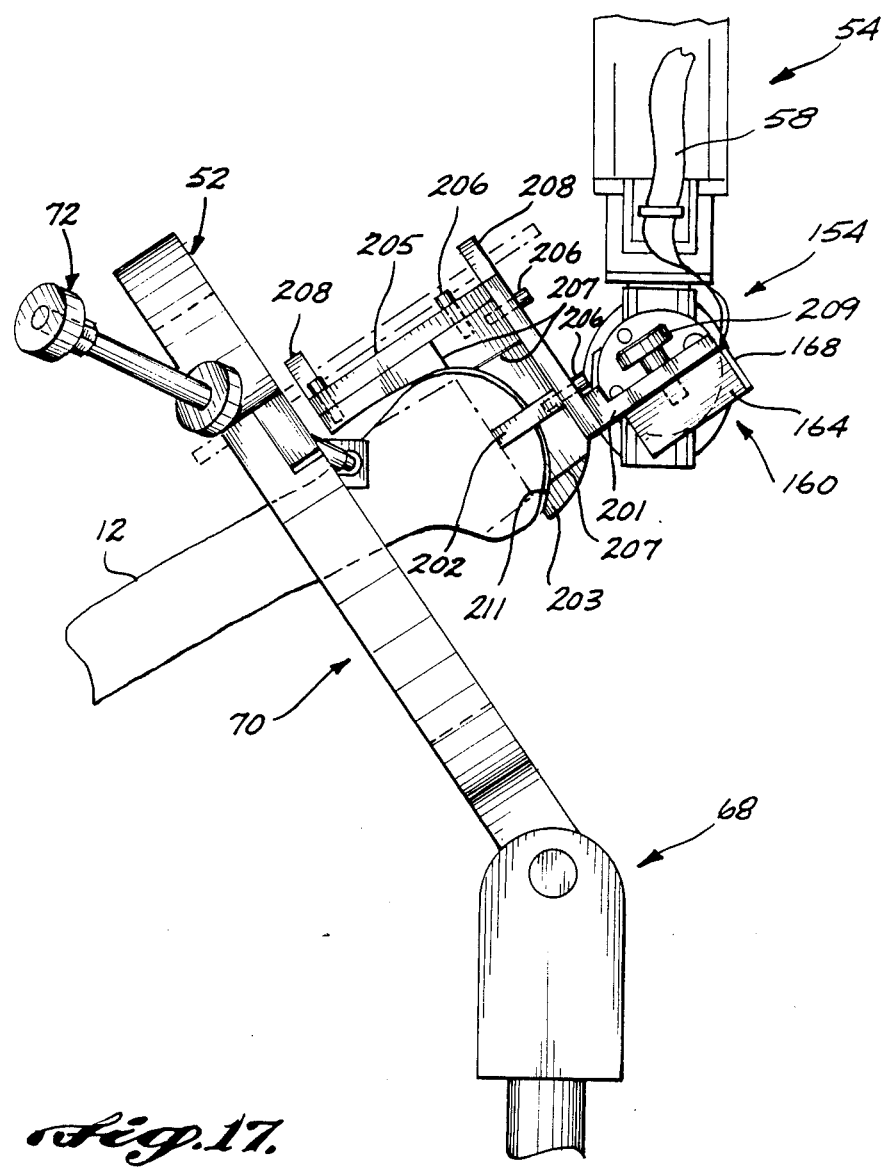
FIG. 17 is a side view of the template attached to the robot and positioned near the end of an uncut bone.

With reference to FIG. 17, the vertical edge 211 closely conforms to a relatively normal femur end. If the bone is damaged, e.g., a large notch exists in the condyle, the edge 211 allows the surgeon to visualize what the prosthesis surface will look like relative to the existing bone. The cut-guide marks are extended in reference through the bone. The cut-guide marks aid the surgeon in visualizing the prosthesis inner surface relative to the template position.

Figure 18:
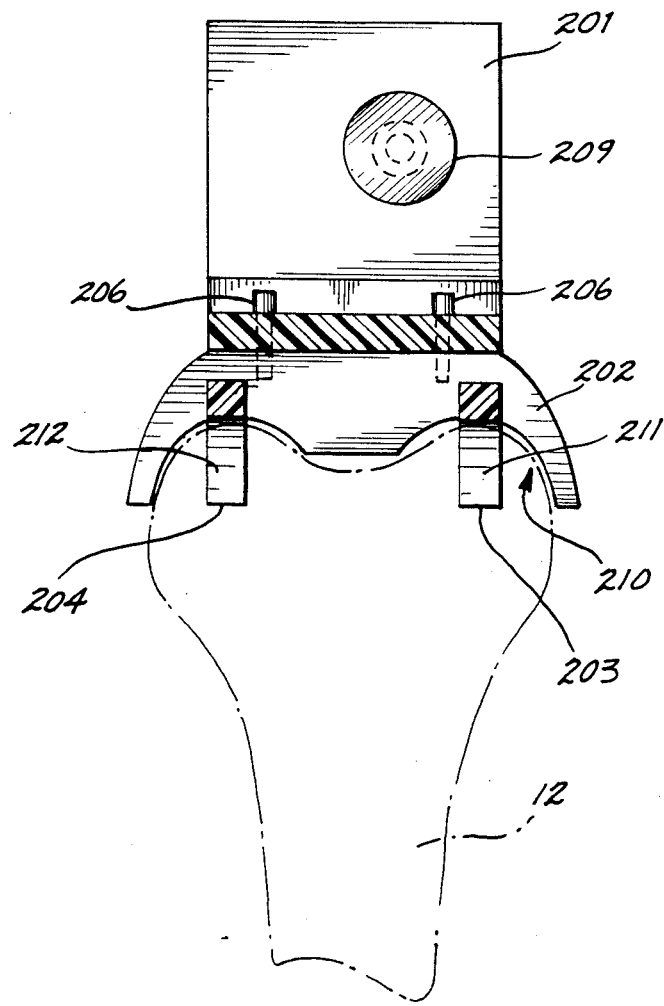
FIG. 18 is a top view of the template with the top portion cut away to show the relationship between the horizontal plate and an uncut bone.

With reference to FIG. 18, the contours of the horizontal plate edge 210 follow a medial-lateral contour line across the distal end of the femur. The positions of the lower portions of the vertical edges 211 and 212 relative to the positions of the concave portions of the horizontal edge provide the surgeon with a variety of reference lines for visualizing the continuous contours of the prosthesis outer surface.

The cut-guide marks and plate edges assit in positioning four degrees of freedom of the prosthesis: anterior-posterior, distal-proximal, and medial-lateral translation; and axial rotation. The alignment rod assists in positioning the flexion-extension and varus-valgus rotations. The template is preferably made of transparent plastics, such as plexiglas, which allow the surgeon to easily visualize the relationship between the femur and the prosthesis by viewing the inner edges of the template and the cut-guide marks.

In operation, the template attachment flange 201 is attached to the coupling block of the coupler and, thus, to the robot by means of thumbscrew 209. The alignment bores (not shown), of the attachment flange are inserted over the alignment studs of the coupling block. The template identification is checked by reading the identification pattern (not shown) on the attachment flange. In one method, the robot arm is then freed from all mechanical locking of the joints, i.e., set to a passive mode, so that the surgeon can manually position the template relative to the femur. The encoders remain active throughout the positioning step. The positioning is a subjective determination by the surgeon aided by the template. The inner edges of the template are positioned in the desired position of the exterior surface of the prosthesis. After the surgeon has positioned the template to his or her satisfaction, the robot is set to the active mode wherein the servomotors are active, and wherein robot movement occurs in response to movement commands received from the controller. The controll than reads the position of the template in the world coordinate system. This reference position is stored in the supervisor memory. An alternative method of positioning the template is to control the movement of the manipulator by some remote means such as the teaching pendant or a joystick so that the robot remains in an active mode throughout the template positioning task.

The bone alteration program may provide an additional positioning aid. Once the template is positioned by the surgeon, either in the passive or active mode, the surgeon may desire an extremely slight adjustment. Rather than physically moving the template, the program can accept a reference position modification command. The modification, e.g., 1 mm translation along the Z-axis defined in the tool coordinate system, is applied to the reference position, and a new reference position is generated which reflects the modified position. Such a position modification procedure is desirable when an x-ray of the positioned template is made and analyzed. Modifications according to the x-ray may be made more exactly through the program than by physically repositioning the template.

An additional decision-making aid can be incorporated into the bone alteration program. An expert system, that uses a knowledge base related to the bone alteration surgery is incorporated into the bone alteration program. For example, a definite and quantitative relationship between the amount of bone removed from the tibia and the varus/valgus flexity of the knee is determinable. By incorporating this and similar relationships into the bone alteration program, the surgeon is advised by the program of the biomedical consequences of the contemplated surgical operation to the bone. The expert system utilizes the reference position established by the procedure to determine the relevant information to be provided to the surgeon. Alternatively, the bone alteration program suggests modifications to the ongoing procedure which would improve the clinical outcome. If the surgeon approves of the suggested modifications, the positioning of surgical tools is modified through the program. These and other bone alteration program modifications and enhancements are made according to the requirements of the specific procedure and the availability of additional information, such as the data necessary to establish an expert system.

One robot safety feature that is available using the bone alteration program is the concept of a "safe sphere." This is an area of a previously defined dimension that surrounds the learned position of the bone. The robot will only enter the sphere if it is commanded to do so, and will move within the sphere only along a straight line; i.e., toward the line corresponding to the approach edge that is defined for each cut and bore defined in the geometric database. When retreating from the safe sphere, the robot will retreat along the same line. Rotational and translational motion of the tool takes place only outside of the safe sphere, thereby protecting the femur and exposed knee from damage caused by inadvertent touching or striking by the tool.

Once the template is positioned in the desired position, and the reference position recorded, the next step in the procedure is to make the bone cuts and/or bores. The tools for the cutting and boring tasks will be immediately described, while the methods for determining the position of and actually positioning the tools will be discussed in a later section.

Figure 19:
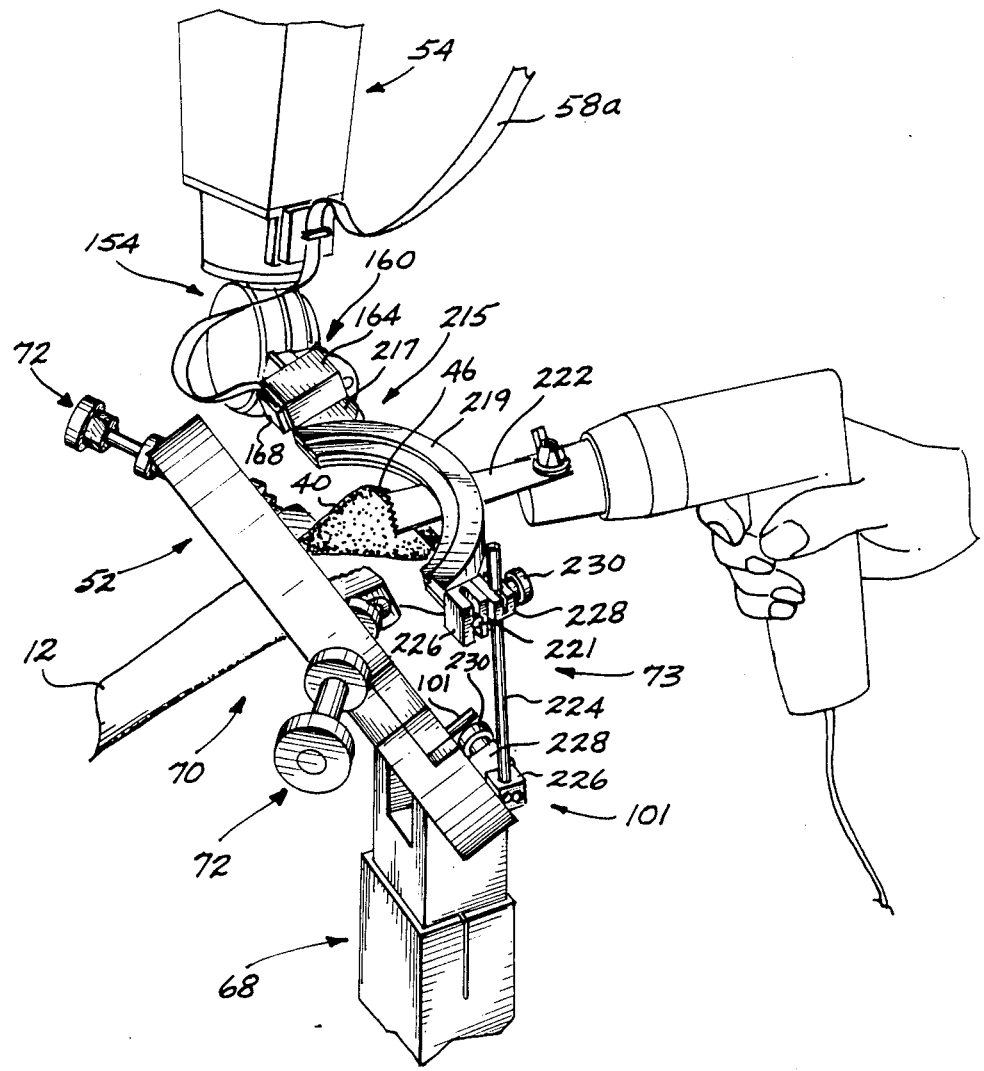
FIG. 19 is an isometric view of a use of the saw guide of the present invention positioned near the immobilized bone.

As illustrated in FIG. 19, saw guide 215 is mounted on coupling block 164 and positioned near the end of the femur. The saw guide includes attachment flange 217 and guide plates 219. In one preferred embodiment, the saw guide is connected by anchor pin 221 to stabilizing device 73. A saw blade 222 is shown in a cutting position.

In one preferred embodiment, the saw guide is crescent shaped so that it can be used near a bone end in a manner that minimally interfaces with the overall view of the bone. The crescent shape allows the guide to be placed relatively close to the bone and allows the saw blade to approach the bone from a range of angles. The surgeon can see the entry point of the blade. While the saw guide is shown positioned and oriented for an anterior cut, the same guide is used to guide the saw blade in each of the cut planes.

A surgical blade fits between and is held in the plane of the guide plates so that the movement of the blade is limited to one plane although the blade is allowed to move freely within the plane. Thus, if damaged bone, blood vessels, flesh, etc. lie in the cut plane, the surgeon is free to manipulate the blade within the cut plane to avoid those specific portions of the knee.

In a preferred embodiment, the system includes a stabilizing device 73 to secure the end of the saw guide that is opposite the attachment flange 217. With a small robot or a robot manipulator with slightly movable joints, it is desirable to provide an additional support for the manipulator. The need for additional support arises from the compliance of the manipulator, limited strength of the servomotors, and/or backlash in the gear trains. The PUMA 200 robot, as an example, is essentially a cantilevered beam extending from its base, so even relatively small forces applied to the saw guide produce movements large enough to overcome the effective stiffness of the robot.

In one preferred embodiment that is additionally illustrated in FIG. 4, the stabilizing device 73 includes a bridge rod 224, two pin block 226 and rod block 228 pairs. One pin block is attached to the immobilizer by stabilizing pin 101 secured into one of a series of bores through the lower frame of the immobilizer, the bores being perpendicular to the frame surface. Alternatively, the bridge rod is connected to the operating table or other device that provides a stable reference point. The other pin block is attached to anchor pin 221. The pin and rod block pairs are joined by thumbscrews 230 that slide through the pin block and screw into the rod block. The pin block can rotate about the thumbscrew. Each block has a bore and slit perpendicular to the thumbscrew. The bridge rod slides through the rod block bores. The blocks are tightened about the pins and rod by the tightening of thumbscrews 230. The pin and rod block pairs, combined with the variety of positions along the frame into which the stabilizing pins 101 can be secured, provide adequate degrees of freedom so that the bridge rod can be connected to the saw guide and the frame regardless of the position of the saw guide.

The necessity of a stabilizer depends on the relative rigidity provided by the device to which the saw guide is mounted. It is beneficial to the accuracy and efficiency of the saw guide to provide a stabilizer for the free end. This benefit is balanced with the time that it takes to adjust and secure the stabilizer during the procedure.

In one preferred embodiment, the stabilizing bridge rod provides an additional safety feature. The saw guide, immobilizer and stabilizer are made of electrically conductive materials and form a simple ground loop detection circuit when the stabilizer is attached to the saw guide and the immobilizer. A portion of the wiring in cable 58a carries signals indicative of the status of the circuit. The signals are received at controller input/output port 60. The controller can determine whether the saw guide, and, thus, the manipulator is rigidly connected to the stabilizer. The bone alteration program checks this circuit status before allowing the saw guide to be moved once it has been positioned adjacent the patient. If a move command is received and the stabilizer circuit is complete, the program generates an error message that indicates that the stabilizer must be detached before the move can be accomplished. The stabilizer is alternatively attached to the operating table or some other structure that is rigidly positioned relative to the reference structure. When the stabilizer is connected to an electrically conductive structure, the safety circuit can be utilized. Additionally, other methods for determining whether the tool is braced, such as an LED detection array or microswitches could be used.

Figure 20:
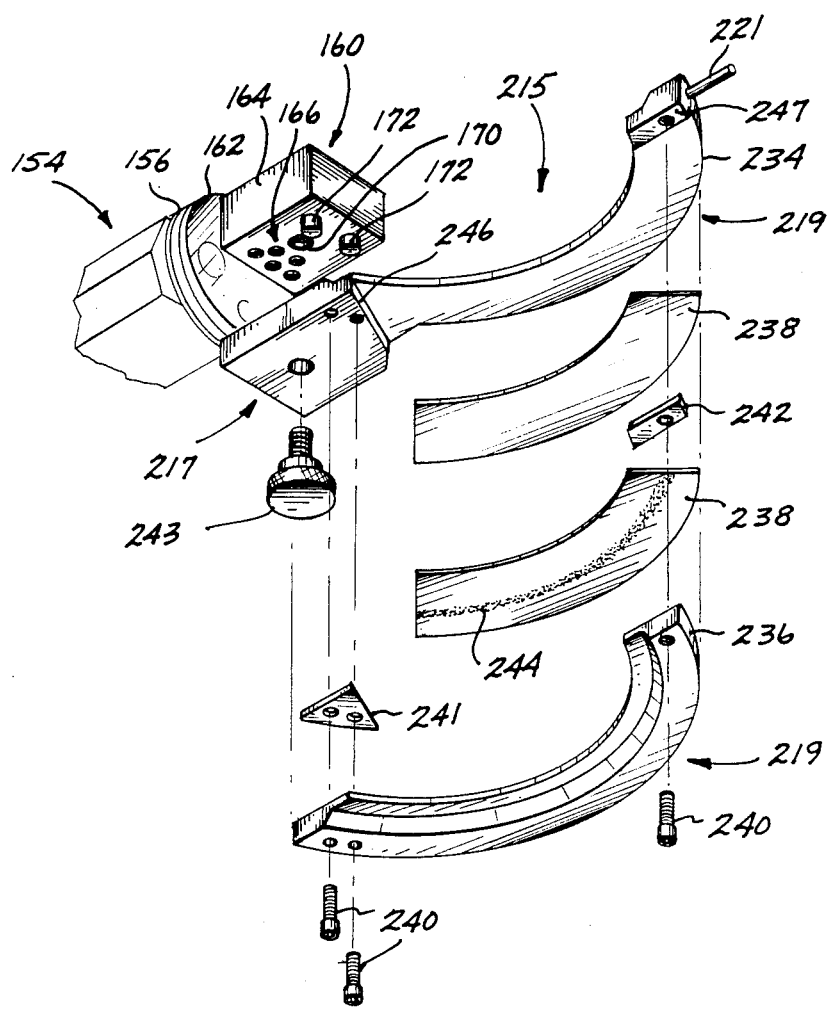
FIG. 20 is an exploded view of the saw guide.

FIGS. 20 through 22 illustrate one preferred construction of the saw guide 215. As shown in FIG. 20, the saw guide includes top plate 234, and bottom plate 236, inner liners 238, connector screws 240, shims 241 and 242 and thumbscrew 243. The attachment flange 217 extends from one end of the top plate. The plates are connected so that the distance between the plates is nearly equal to the thickness of the saw blade chosen for the operation.

The top and bottom plates are made of a rigid material, preferably stainless steel or other material that is suitable for use in the surgical environment. The liners 238 are preferably made of a low-friction material, such as Teflon. In one embodiment, the liners are permanently bonded to the plates by epoxy. Alternatively, the liners are provided with a strip of adhesive 244 to attach them to the plates. The latter guide liners are preferably disposable to avoid the need to resterilize them as well as to avoid wearing of the liners which may result in residue from the liners falling into the exposed area. By using adhesive strips 244, the liners can be easily attached and removed from the plates.

The guide liners are shaped to conform closely to the curve and radial dimensions of the inner surfaces of the top and bottom plates. As shown in FIGS. 20 and 21, the length of the liners is slightly shorter than the top and bottom plates so that slight recesses 245 are left between the plates at each end of the guide curve. The recesses are useful when the teeth of the blade are slightly offset from the plane of the blade so that it is difficult to pass the teeth between the lined plates. The toothed edge of the blade is passed between one of the end recesses to position the blade for cutting. The liners extend far enough to the guide ends so that the recesses are not large enough to allow the blade to slip outside of the lined area. Alternatively, the ends of the guide plates remote from the attachment flange are not connected together. The saw blade then slides through this opening. A suitably rigid material must be used for the guide plates in this configuration.

A default blade thickness capacity is dictated by the height of ledges 246 and 247 on the top plate and the thickness of the liners. The distance between the plates can be increased to accommodate blades of various thicknesses. One or more shim pairs 241 and 242 can be inserted between the top and bottom plates to increase the distance between the liners. The shims are secured between the guide plates by connector screws 240.

With reference to FIGS. 21 and 22, pin guides 248 extend through the top and bottom plates and are suitable for receiving pins 249. The pin guides lie in the plane of the guide plates. The pins provide an alternative saw guide stabilizing means. The pins can be strategically positioned through the saw guide and tapped into the bone to secure the guide relative to the bone. The pins do not interfere with the cut plane or with the surgeon's view of the area.

Figure 23:
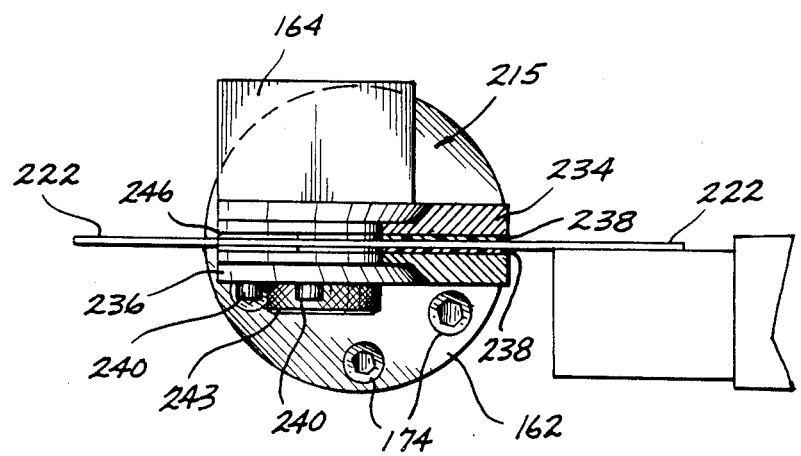
FIG. 23 is a side sectional view of the saw guide illustrated in FIG. 21 with a section taken along line 23 and a saw blade positioned between the guide plates.

As shown in FIG. 23, the saw blade fits snugly between liners 238. The guide plates and attachment flange do not obstruct the view of the cutting edge of the blade which extends beyond the guide plates.

Figure 24:
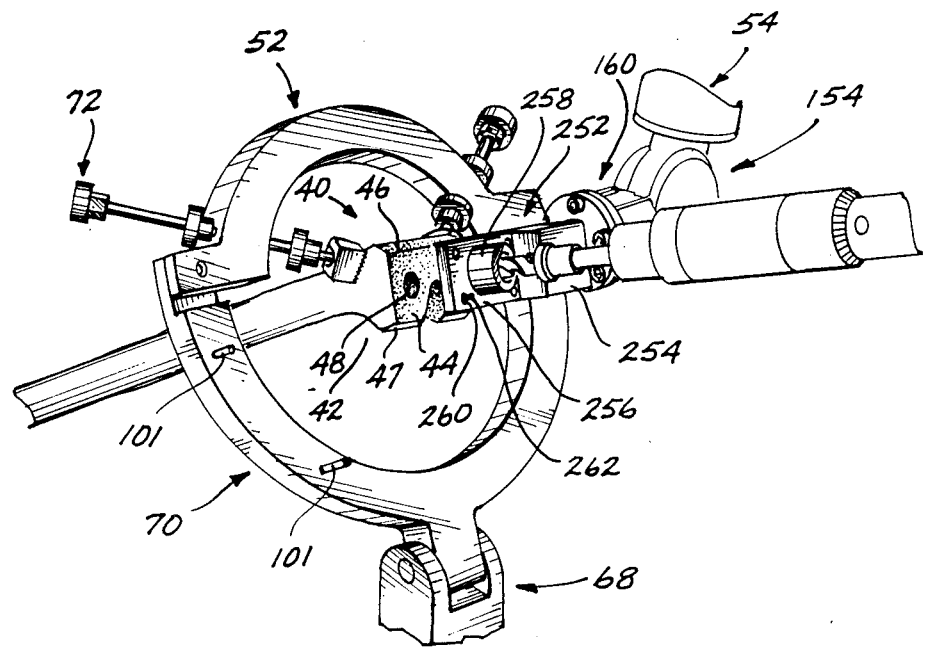
FIG. 24 is an isometric view of a use of the drill guide of the present invention positioned near the immobilized bone.

FIG. 24 illustrates a drill guide 252 used in the present system. The drill guide includes an attachment flange 254, a reference plate 256, a threaded bit guide 258, and pin guides 260. The reference plate is perpendicular to the axis of the bit guide 258. The attachment flange of the drill guide is similar to that of the saw guide, with the identification pattern identifying it as a drill guide. The attachment flange is connected to the coupling block by a thumbscrew (not shown). Preferably the bores are made after the distal cut, but that is not required. The bit guide axis need only be aligned with the bore axis and the guide positioned near the bone to successfully complete the drilling task. Bit fitters of different diameters are available and can be screwed into the bit guide so that the drill guide can be used with a variety of bit sizes.

Once the drill guide is attached to the robot and the identification checked, the robot positions the guide for the specific bore, i.e., medial, lateral, center, etc., according to the surgeon's choice. The robot positions the drill guide so that the reference plate is against the distal end of the bone. Once the drill guide is positioned, it is further stabilized by tapping pins 262 through pin guides 260. Alternatively, the unattached drill guide is positioned manually and secured by pins or other stabilizing means.

Once the drill guide is in place, the bore is drilled. Often, the depth of the drill is gauged by a notch on the bit itself that corresponds to the length of the bore plus the length of the bit guide. Obviously, the mark must also take into account whether the guide is to be positioned before or after the distal cut is made. Each additional drilling task is carried out in a similar manner.

The integration of the template, saw guide, and drill guide into a robot-aided bone alteration surgery will now be described.

Figure 25:
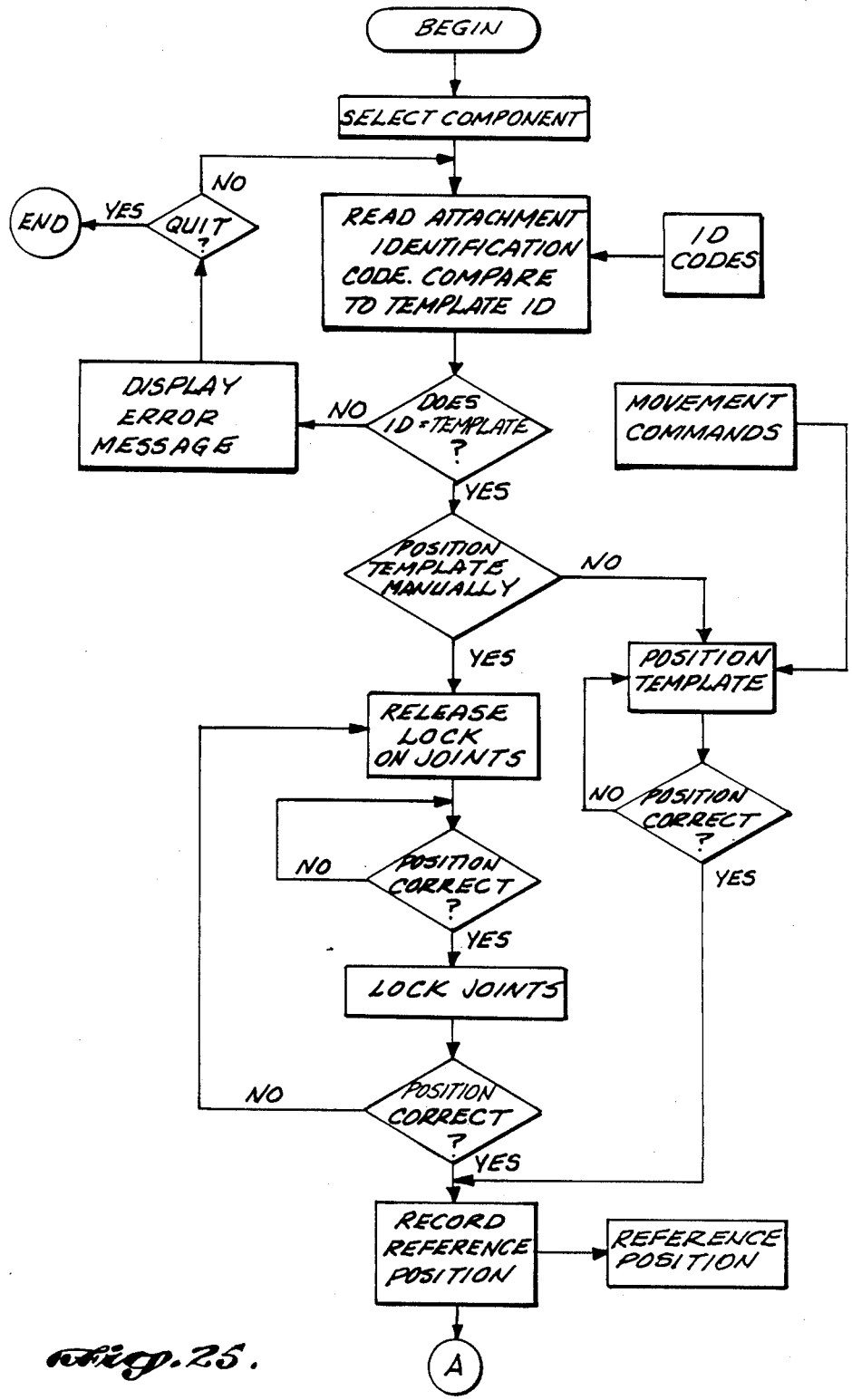
FIG. 25 is a flow diagram of the method of the present invention for determining the desired position and orientation of a prosthesis relative to a bone.

Once the leg is situated through the immobilization device, the knee is opened and the femur immobilized. The robot is then taught the desired task position on the femur. In a TKA, the task position corresponds to the desired prosthesis position. Referring now to the flow chart of FIG. 25, the bone alteration program is initiated on the supervisor. At those steps in the program where the surgeon is provided with options, the choice is indicated during surgery by the surgeon touching the TouchWindow screen at a point corresponding to the option.

The first step is to choose a task, which, in the instance of a TKA, requires choosing a prosthesis. This is done at the select component step. The corresponding prosthesis template is mounted on the coupler as described above. The identification pattern on the template attachment flange is checked against an identification code database in the supervisor. The identification pattern is obtained by polling the signal from the identification component at the input/output port. If the identification code is correct, the control system moves onto the next step. If the identification is incorrect, the control system will signal an error to the surgeon, and allow the surgeon to quit the program or to proceed once the proper template is attached.

Once the template is attached, the prosthesis task or position is taught to the robot. In the preferred method, the robot is switched to a passive mode wherein the robot manipulator is manually manipulated. In the passive mode the servomotors in the robot joints are unpowered and the incremental encoders in the joints are still active. The passive mode is provided by the manufacturer to be used during the extraction of a robot manipulator from a difficult crash situation. However, in this system, the robot is placed in the passive mode and the surgeon is allowed to control the template position manually by manipulating the robot manipulator.

Since the immobilization device allows the knee to be established in a variety of positions, there is no method for preprogramming the robot to move the template to the proper position relative to the femur end. However, alternative, nonmanual movement control methods, such as using the teach pendant or a joystick, could be used. The preferred method is advantageous because it is relatively quick and allows the surgeon a great deal of control over the precise position of the template without the necessity of generating a number of movement commands through the controller.

Once the template is positioned, the joints are locked so that the position can be considered by the surgeon. The unlocking and relocking step is repeated until the position of the template is considered satisfactory. Once a satisfactory position is obtained and the position locked, the surgeon indicates that the template position should be recorded. The robot position sensors then transmit to the controller the position of the template in the world coordinate system.

Figure 26:
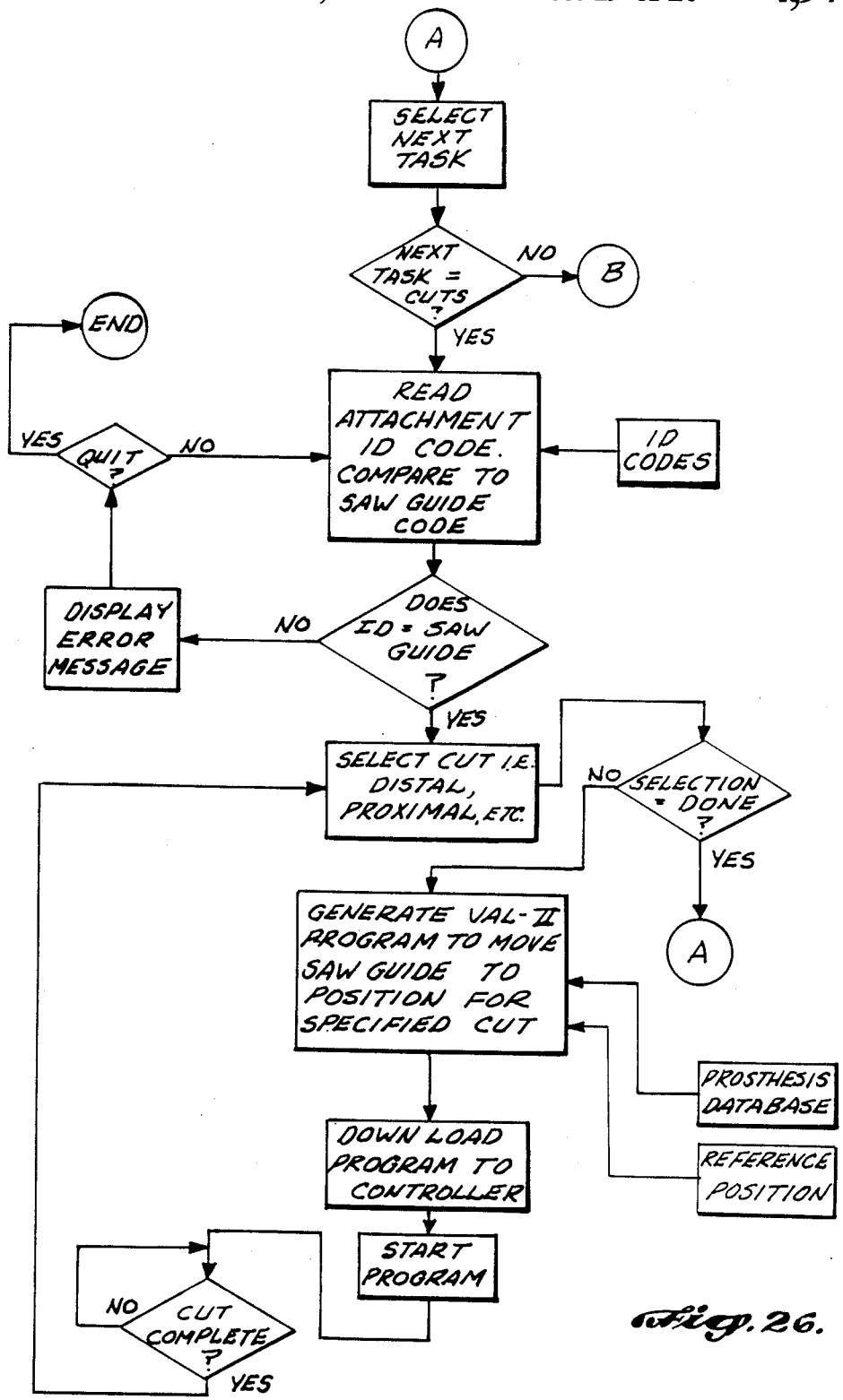
FIG. 26 is a flow diagram of the method of the present invention for determining the position and orientation of a saw guide relative to the desired position of the prosthesis.
Figure 27:
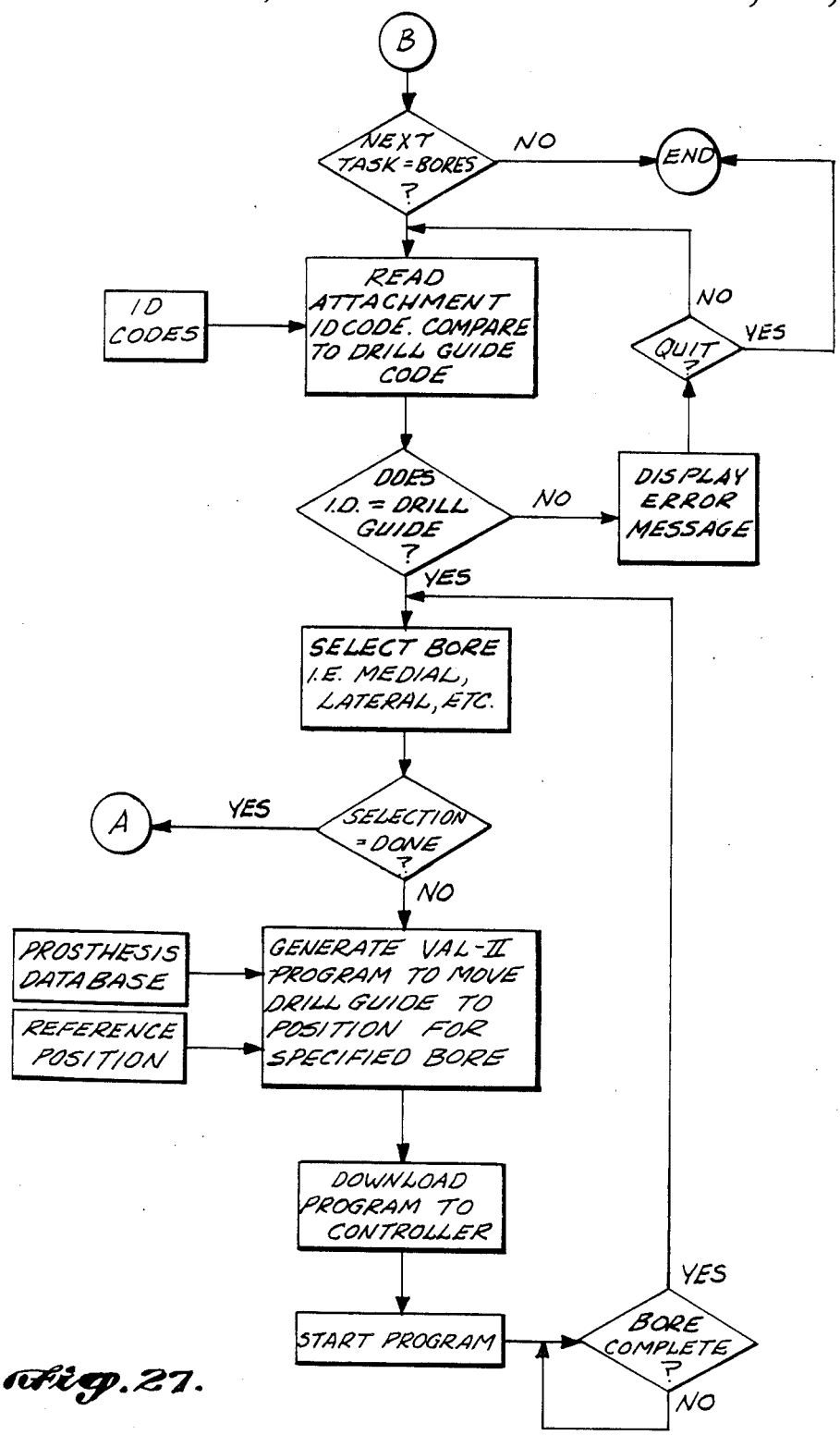
FIG. 27 is a flow diagram of the method of the present invention for determining the position and orientation of a drill guide relative to the desired position of the prosthesis.

With reference to FIGS. 26 and 27, the next step is to cut or bore the bone. Once the cut task is chosen, the tool identification code is read to determined whether the saw guide has been attached. If the guide has not been mounted then an error is indicated to the surgeon. Once the saw guide is attached, the surgeon chooses the order of the cuts by choosing a cut type on the input screen. Once a cut is chosen, such as the anterior cut, the control system uses conventional geometric transformations to integrate the anterior plane coordinates from the geometric database with the reference position to determine the anterior cut plane position in the world coordinate system. Then, working in a reverse manner, the tool position in the world coordinate system for the anterior cut is determined by combining the cut plane position with the tool definition. The result is a position array corresponding to the proper position of the tool in the world coordinate system that will position the saw guide for the anterior cut. The bone alteration program generates or provides variable values to a VAL-II program that is downloaded to the controller. The controller processes the program and the robot positions the saw guide accordingly.

As discussed above, once the saw guide is positioned, a stabilizing device is used to provide additional rigidity to the tool position. After the cut is made and the stabilizing device is disconnected, the robot is commanded to move to the next step.

The surgeon continues to command the robot to move the saw guide to the proper position for each of the cuts necessary for the bone preparation. Using this method, the surgeon is free to choose the order of the cuts.

With reference to FIG. 27, once the surgeon has indicated that boring will be the next step, the bone alteration program will ascertain whether the drill guide has been attached to the coupling block. If the tool has been properly attached, the surgeon will be allowed to continue. The surgeon decides which bore is to be drilled first, and indicates the choice through the input screen. The program then determines the position of the drill guide in a manner similar to the determination of the saw guide position described above. A VAL-II program is generated, downloaded to the controller, and executed. The robot will then move the drill guide to the appropriate position adjacent the femur. Once the guide is flush against the distal cut, it is preferable to stabilize the guide with reference to the bone to prevent slight movements during the boring procedure. The bone is then drilled out, the stabilizing device is disconnected, and the robot is commanded to move to the next step. If more than one bore is to be made in the bone, each bore is made sequentially according to the order chosen by the surgeon.

Once the bores are completed, the femur preparation task is done and the robot returns to its resting position. The area of the knee is then cleaned out and the prosthesis attached to the femur. The knee is then sewn up.

A number of safety features are available using the present invention. One programmable safety feature is to command the robot through the bone alteration program to position the tool a predetermined distance away from the bone, such as 10 cm, rather than commanding the robot to initially position the tool in what is calculated to be the desired position. For example, during a cutting procedure, the bone alteration program generates a tool position command that will place the tool relatively near the femur. The program then adds a translational distance to one of the coordinates of the position so that the saw guide is initially oriented in the proper plane, but is positioned a predetermined distance away from the femur. The translation is along the same coordinate axis along which the tool moves in the safe sphere. The surgeon then uses the input screen to move the tool closer to the bone in incremental steps until the surgeon is satisfied with the bone-tool relationship. The initial position of the tool will be within the safe sphere so that all movement closer to the bone will be in a plane and no rotation of the tool will be done. Thus, the surgeon can position the tool at the most advantageous position for the specific cut. Additionally, using this method, the robot is not relied upon to make contact type positioning such as placing the drill guide flush with the distal cut.

The safety stand and stabilizer circuit allow for automated continuous polling of the status of the robot. During robot movement, the controller continuously polls the signals on cable 58b connected to the robot safety stand. If the signals indicate that the stand has tilted enough to break one of the circuits then the supervisor will shut off power to the robot so that all movement ceases. Additionally, when a movement command is received during the bone cutting procedure, the controller polls the signals on Cable 58a connected to the mounting flange. If the signals indicate that the robot is attached to the stabilizer, the program will not allow a move command to be executed. This prevents the manipulator from moving when it is secured to another structure.

The present invention has been described in terms of a TKA procedure. It is to be understood that the system of the present inventions can be applied in many procedures. The one aspect of the system that must be modified to match a specific procedure is the configuration of the template. The template used in each specific procedure is used to teach the robot the position and orientation of some aspect of the procedure.

For example, the system is applicable to osteotomy and ligament repair procedures. In an osteotomy, a wedge of bone is removed from one side of a bone so that the bone is shortened on that side. The cut areas are then brought together so as to change the axis of the bone. The surgeon must determine the area of the bone from which the wedge is to be removed and additionally determine the dimensions of the wedge. An elongated template having a side that represents the exterior surface of the bone is one suitable template. The template includes a center mark that is aligned by the surgeon with the center of the wedge. The template also includes a vertex pointer. Thus, features of the template indicate the desired position of the center of the wedge surface and of the vertex. The geometric database for the osteotomy includes the geometric relationships between the two cut planes that define the wedge. The position of the cut planes will be relative to some point and orientation of the template. As in the TKA procedure, the leg would be immobilized and the area of the surgery exposed. Once the template is positioned relative to the bone, the reference position is recorded. The surgeon then indicates to the program the angles of the wedge to be cut. Using the angle data and reference position, the robot can be commanded to position a saw guide for each cut of the wedge. The cuts are positioned symmetrically about the point or line on the bone that was indicated by the center mark on the template. The above-described bone alteration surgical task would be run. At the "DO select" action, an osteotomy would be chosen. The "DO holes" action would not be necessary. The task would execute the appropriate VAL-II program for an osteotomy.

In one type of ligament repair, a bore is drilled completely through a bone or set of bones, and ligament material is stretched through the bone and secured. One template configuration useful for such a procedure is a pointer. The pointer tip represents the position of a bore end relative to the bone. The pointer is used to indicate two reference points. The geometric database for ligament repair includes a line that relates to the template point feature in that the line extends between the two reference points. Again, the leg is immobilized and the area for surgery is exposed. The template is then positioned so that the tip of the template points to or rests on the bone area, first at one bore end and then at the other. Each position is recorded. The program then determines the proper position and orientation of the drill guide mounted to the robot mounting flange for carrying out the drilling task so that the bore extends between the two bore entry points. The above-described bone alteration surgical task would again be run. A ligament repair procedure would be chosen, and only the "DO bores" action would be available. A VAL-II program is generated at the "DO cuts" action, the program is downloaded and executed to move the tool to the proper position.

While preferred embodiments of the invention have been illustrated and described, it will be appreciated that various changes can be made therein without departing from the spirit and scope of the invention. For example, a variety of robots, controllers and supervisors could implement the system. The system can be used for other bone alteration procedures by using appropriate templates. Additionally, the tool identification device could utilize Hall-effect switches, microswitches, or other methods for carrying out proximity detection.

The embodiments of the invention in which an exclusive property or privilege is claimed are defined as follows:

1. A system for positioning a tool relative to a patient's bone to facilitate the performance of a surgical bone alteration task, the system comprising:
   bone immobilization means for supporting the bone in a fixed position with respect to a reference structure;
   a robot comprising a base fixed in position with respect to the reference structure, a mounting member, a manipulator connected between said base and said mounting member and permitting relative movement therebetween, and attachment means for securing the tool to said mounting member; and
   means for causing said mounting member to move relative to the reference structure in response to movement commands, whereby the tool can be moved to a desired task position to facilitate performance of said task.

2. A system as claimed in claim 1, further including task control means for controlling and monitoring the operation of said robot, said task control means comprising memory means for storing data and control programs, and control-processing means for processing said control programs to generate said movement commands.

3. A system as claimed in claim 2, further comprising a template attachable to said mounting member, and means for recording a reference position of said template when said template is positioned such that a feature of said template is in a desired position relative to the bone, said reference position being recorded in a world coordinate system that is fixed with respect to the reference structure.

4. A system as claimed in claim 3, wherein said data in said memory means includes a geometric database comprised of data representative of the geometric relationships relevant to performance of the task, and wherein the task control means includes a tool-positioning program for determining the task position in said world coordinate system by integrating said geometric database and said reference position, and for generating movement commands for directing the mounting member to a position such that the tool secured to the mounting member is in the task position.

5. A system as claimed in claim 4, wherein the tool includes a tool identification pattern and wherein said attachment means includes an identification device positioned so as to be adjacent said identification pattern when the tool is secured to said mounting member, said identification device including means for ascertaining said tool identification pattern and generating signals indicative thereof, said task control means including means for identifying the tool attached to said mounting member by actuating said identification device and interpreting said identification signals.

6. A system as claimed claim 5, wherein said identification device includes a plurality of LED photodetector pairs, said photodetector pairs being capable of transmitting and receiving radiation signals, and said tool identification pattern is a plurality of bored and unbored areas such that when the tool is mounted on said mounting member and said photodetectors are actuated, a reflected signal will be detected by said photodectors when they are adjacent a bored area and will not be detected when said photodetectors are adjacent an unbored area, whereby said identification signals are indicative of reflected and nonreflected signals.

7. A system as claimed in claim 4, wherein said robot base includes a safety stand that tilts the robot if the robot encounters a rigid object while it is moving, and that generates a safety signal when said stand tilts, whereby said task control means responds to said safety signal by preventing further movement of the robot.

8. A system as claimed in claim 3, wherein said task control means further comprises operator interface means for displaying system information and receiving data and operator control commands, wherein said robot includes position-sensing means for generating positional signals indicative of the position of said mounting member in the world coordinate system, and means for operating in a passive mode in which the mounting member may be moved manually by an operator, and wherein the task control means first sets said robot to the passive mode and then, upon receiving an operator command indicating that said template has been positioned in a desired position, records said reference position and sets said robot to an active mode in which the mounting member moves in response to said movement commands.

9. A system as claimed in claim 2, further comprising a template attachable to said mounting member, a feature of said template representing a portion of a prosthesis, and means for recording a reference position of said template when said template is positioned such that said feature is in a desired position relative to the bone, the reference position being recorded in a world coordinate system that is fixed with respect to the reference structure.

10. A system as claimed in claim 9, wherein said data in said memory means includes a prosthesis database comprised of data representative of the geometric relationships defining one or more interior surfaces of the prosthesis, and wherein said task control means includes a tool-positioning program for determining the task position in the world coordinate system by integrating said prosthesis database and said reference position, and for generating movement commands for directing the mounting member to a position such that the tool secured to the mounting member is in the task position.

11. A system as claimed in claim 10, wherein the tool includes a tool identification pattern and wherein said attachment means includes an identification device positioned so as to be adjacent said identification pattern when the tool is secured to said mounting member, said identification device being suitable for ascertaining said tool identification pattern and generating signals indicative thereof, said task control means including means for identifying the tool attached to said mounting member by actuating said identification device and interpreting said identification signals.

12. A system as claimed claim 11, wherein said identification device includes a plurality of LED photodetector pairs, said photodetector pairs being capable of transmitting and receiving radiation signals, and said tool identification pattern is a plurality of bored and unbored areas such that when the tool is mounted on said mounting member and said photodetectors are actuated, a reflected signal will be detected by said photodetectors when they are adjacent a bored area and will not be detected when said photodetectors are adjacent an unbored area, whereby said identification signals are indicative of reflected and nonreflected signals.

13. A system as claimed in claim 10, wherein said base includes a safety stand that tilts the robot if the robot encounters a rigid object while it is moving and generates a safety signal when said stand tilts, and wherein said task control means includes means for responding to said safety signal by shutting off power to said robot.

14. A system as claimed in claim 10, further includes stabilizing means for providing a rigid link between said mounting member and the reference structure in addition to the link provided by said manipulator.

15. A system as claimed in claim 14, wherein said stabilizing means provides a detectable link with said manipulator, and said task control means includes means for detecting said link.

16. A system for determining a reference position of a template relative to a patient's bone to facilitate the performance of a surgical bone alteration task, the system comprising:
bone immobilization means for supporting the bone in a fixed position with respect to a reference structure;
a robot comprising a base fixed in position with respect to the reference structure, a mounting member, a manipulator connected between said base and said mounting member and permitting relative movement therebetween, attachment means for securing the template to said mounting member, position-sensing means for generating positional signals indicative of the position of said mounting member in a world coordinate system that is fixed with respect to the reference structure; and
means for operating said robot in a passive mode in which the mounting member may be moved manually by an operator, whereby the template can be moved to the reference position.

17. A system as claimed in claim 16, further comprising task control means for controlling and monitoring the operation of said robot, said task control means comprising memory means for storing data and control programs, whereby the reference is recorded by said task control means.

* * * * *

UNITED STATES PATENT AND TRADEMARK OFFICE
CERTIFICATE OF CORRECTION

PATENT NO. : 4,979,949

DATED : December 25, 1990

INVENTOR(S) : Frederick A. Matsen et al.

It is certified that error appears in the above-identified patent and that said Letters Patent is hereby corrected as shown below:

| Column | Line | Error |
|---|---|---|
| 3 | 63 | After "of" insert --total-- |
| 4 | 18 | Delete "per cent" and insert therefor --percent-- |
| 4 | 58 | Delete "alternation" and insert therefor --alteration-- |
| 16 | 46 | Delete "NCMOS" and insert therefor --(CMOS)-- |
| 19 | 42 | Delete "scrip" and insert therefor --script-- |
| 20 | 53 | After "of all" insert --list members to be certain the file is complete. A variety of methods are known for performing such geometric integrity checks. One method is to solve for the normal vector of the plane, determined by the first three constituent points encountered, and then to check the dot product of the normal vector with the vector defined by each subsequent point. If the product is nonzero, the point if outside of the plane. The tightness of the press fit can be modified, if desired, by modifying the information in the geometric database. For example, if it is desirable to cut the femur end so that it is slightly larger than the prosthesis' inner surface, as is the current practice, the data corresponding to the surface-cut relationships will be altered so that the cut positions are adjusted away from the proximal end of the femur. This data adjustment is entered in the database prior to the performance of the procedure so that no adjustments need be made during the TKA. Programs are written in VAL-II and stored in the supervisor or controller for use by the main surgical program. These contain the commands for specific procedural steps such as positioning a tool in a cut plane, moving the mounting flange to the nest, etc. The VAL-II programs can then be accessed by the main program during the procedure. The VAL-II programs, when accessed, are downloaded to the controller and executed. |

UNITED STATES PATENT AND TRADEMARK OFFICE
CERTIFICATE OF CORRECTION

Page 2 of 3

PATENT NO. : 4,979,949

DATED : December 25, 1990

INVENTOR(S) : Frederick A. Matsen et al.

It is certified that error appears in the above-identified patent and that said Letters Patent is hereby corrected as shown below:

| Column | Line | Error |
|---|---|---|
| | | In one preferred embodiment, the main surgical bone alteration program is written in a high level language as a task. A task program is of the form:<br>    TASK task name<br>    action 1<br>    action 2<br>    .<br>    .<br>    .<br>Types of actions include:<br>    DO a subtask<br>    MAKE a named cut or hole<br>    POSITION a template attached to the robot wrist<br>    DEFINE a prosthesis' geometry database source<br>    DEFINE a named cut or hole as a named feature of a template<br>One sample bone alteration surgical task that could control a bone alteration surgery is:-- |
| 22 | 7 | Delete "assit" and insert therefor --assist-- |

UNITED STATES PATENT AND TRADEMARK OFFICE
CERTIFICATE OF CORRECTION

PATENT NO. : 4,979,949

DATED : December 25, 1990

INVENTOR(S) : Frederick A. Matsen, et al.

It is certified that error appears in the above-identified patent and that said Letters Patent is hereby corrected as shown below:

| Column | Line   |                                                                                     |
|--------|--------|-------------------------------------------------------------------------------------|
| 22     | 36, 37 | Delete "con-troll" and insert therefor --controller--                               |
| 30     | 46     | Delete "photodectors" and insert therefor --photodetectors--                        |

Signed and Sealed this

Fifteenth Day of September, 1992

Attest:

DOUGLAS B. COMER

Attesting Officer     Acting Commissioner of Patents and Trademarks